US011369669B2

(12) United States Patent
Czink et al.

(10) Patent No.: US 11,369,669 B2
(45) Date of Patent: Jun. 28, 2022

(54) MEASLES VIRUS ENCODING A TUMOR ANTIGEN

(71) Applicant: Ruprecht-Karls-Universitat Heidelberg, Heidelberg (DE)

(72) Inventors: Elena Czink, Heidelberg (DE); Christine Engeland, Heidelberg (DE); Guy Ungerechts, Heidelberg (DE)

(73) Assignee: RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 664 days.

(21) Appl. No.: 15/784,895

(22) Filed: Oct. 16, 2017

(65) Prior Publication Data

US 2018/0110848 A1 Apr. 26, 2018

(30) Foreign Application Priority Data

Oct. 17, 2016 (JP) ................................ 2016-203835

(51) Int. Cl.

*A61K 48/00* (2006.01)
*C12N 15/85* (2006.01)
*A61K 39/00* (2006.01)
*C12N 7/00* (2006.01)
*A61P 35/00* (2006.01)
*C07K 14/47* (2006.01)

(52) U.S. Cl.

CPC ...... *A61K 39/0015* (2013.01); *A61K 39/0011* (2013.01); *A61K 39/00114* (2018.08); *A61K 39/00117* (2018.08); *A61K 39/00119* (2018.08); *A61K 39/001104* (2018.08); *A61K 39/001106* (2018.08); *A61K 39/001109* (2018.08); *A61K 39/001112* (2018.08); *A61K 39/001113* (2018.08); *A61K 39/001124* (2018.08); *A61K 39/001129* (2018.08); *A61K 39/001156* (2018.08); *A61K 39/001166* (2018.08); *A61K 39/001182* (2018.08); *A61K 39/001186* (2018.08); *A61K 39/001188* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 48/005* (2013.01); *A61P 35/00* (2018.01); *C12N 7/00* (2013.01); *A61K 2039/5256* (2013.01); *C07K 14/4748* (2013.01); *C12N 2760/18434* (2013.01); *C12N 2760/18441* (2013.01); *C12N 2760/18471* (2013.01); *C12N 2799/021* (2013.01); *C12N 2799/04* (2013.01)

(58) Field of Classification Search

None

See application file for complete search history.

(56) References Cited

U.S. PATENT DOCUMENTS

| | | | | |
|---|---|---|---|---|
| 5,591,828 A | 1/1997 | Bosslet et al. | | |
| 6,896,881 B1 * | 5/2005 | Russell | C07K 14/485 | 424/192.1 |
| 9,005,925 B2 * | 4/2015 | Tangy | C12N 7/00 | 435/70.3 |

FOREIGN PATENT DOCUMENTS

| | | | |
|---|---|---|---|
| DE | 2 669 381 | A2 * | 12/2013 |
| EP | 0404097 | A2 | 12/1990 |
| JP | 2003527122 | A | 9/2003 |
| JP | 2009501520 | A | 1/2009 |
| WO | 1993/01161 | A1 | 1/1993 |
| WO | 01/70032 | A1 | 9/2001 |
| WO | 2007/011711 | A2 | 1/2007 |
| WO | 2015/128313 | A1 | 9/2015 |

OTHER PUBLICATIONS

Parks et al., J Virology, Jan. 2001; 75(2)910-920 (Year: 2001).*
Msaouel et al., Expert Opin Biol Ther. 2013, 13(4)1-28 (Year: 2013).*
Allen et al., "Retargeted Oncolytic Measles Strains Entering via the EGFRvIII Receptor Maintain Significant Antitumor Activity against Gliomas with Increased Tumor Specificity", Cancer Res., 2006, 66(24); pp. 11840-11850.
Andtbacka et al. J. Clin. Oncol. 2013, 31, suppl; abstr LBA9008.
Bernardeau et al., "A simple competitve assay to determine peptide affinity for HLA class II molecules: A useful too for epitope prediction", J. Immonoloical Methods, 2011, 371; pp. 97-105.
Andrew J. Bordner "Towards Universal Structure-Based Prediction of Class II MHC Epitopes for Diverse Allotypes", PLoS ONE, 2010, vol. 5, Issue 12, e14383.
Bossow et al., "Armed and targeted measles virus for chemovirotherapy of pancreatic cancer", Cancer Gene Ther., 2011, 18(8):598-608.
G. Galfre and C. Milstein "Preparation of Monoclonal Antibodies: Strategies and Procedures", Methods in Enzymology, 1981, vol. 73, pp. 3-46.
Grossardt et al., "Granulocyte-Macrophage Colony-Stimulating Factor-Armed Oncolytic Measles Virus Is an Effective Therapeutic Cancer Vaccine", Human Gene Therapy, 2013, 24:644-654.
Hammond et al., "Single-Chain Antibody Displayed on a Recombinant Measles Virus Confers Entry through the Tumor-Associated Carcinoembryonic Antigen", J. Virol. 2001, vol. 75, No. 5, pp. 2087-2096.

(Continued)

*Primary Examiner* — James D Schultz
(74) *Attorney, Agent, or Firm* — J.A. Lindeman & Co. PLLC

(57) ABSTRACT

The present invention relates to a recombinant virus of the family Paramyxoviridae comprising an expressible polynucleotide encoding at least one of (i) a tumor antigen, (ii) a fragment of a tumor antigen, and (iii) a variant of (i) or (ii). The present invention further relates to a polynucleotide encoding said recombinant virus of the family Paramyxoviridae and to a host cell comprising said recombinant virus of the family Paramyxoviridae and/or said polynucleotide encoding said recombinant virus of the family Paramyxoviridae. Moreover, the present invention relates to a method for activating immune cells with antitumor activity in a sample comprising cancer cells and to further means, methods, and uses related to the present invention.

9 Claims, 3 Drawing Sheets

Specification includes a Sequence Listing.

(56) References Cited

OTHER PUBLICATIONS

Hasegawa et al., "Affinity Thresholds for Membrane Fusion Triggering by Viral Glycoproteins", J. Virol., 2007, vol. 81, No. 23, pp. 13149-13157.
Heo et al., "Randomized dose-finding clinical trial of oncolytic immunotherapeutic vaccinia JX-594 in liver cancer", Nat. Med., 2013, 19(3):329-336.
Holliger et al., "Diabodies":Small bivalent and bispecific antibody fragments, Proc. Natl. Acad. Sci., 1993, vol. 90, pp. 6444-6448.
Peter J. Hudson and Christelle Souriau "Engineered antibodies", Nature Medicine, 2003, vol. 9, No. 1, pp. 129-134.
Kaufmann et al., "Chemovirotherapy of Malignant Melanoma with a Targeted and Armed Oncolytic Measles Virus", J. Investigative Dermatology, 2013, vol. 133, pp. 1034-1042.
G. Kohler and C. Milstein "Continuous cultures of fused cells secreting antibody of predefined specificity", Nature, 1975, vol. 256, pp. 495-497.
Liu et al., "Prostate-Specific Membrane Antigen Retargeted Measles Virotherapy for the Treament of Prostate Dancer", Prostate, 2009, 69(10): 1128-1141.
Melcher et al., "Thunder and Lightning: Immunotherapy and Oncolytic Viruses Collide", American Society of Gene & Cell Therapy, 2011, vol. 19, No. 6, pp. 1008-1016.
Nakamura et al., "Antibody-targeted cell fusion", Nature Biotechnology, 2004, vol. 22, No. 3, pp. 331-336.
Nielsen et al., "Improved prediction of MHC class I and class II epitopes using a novel Gibbs sampling approach", Bioinformatics, 2004, vol. 20, No. 9, pp. 1388-1397.
Peng et al., "Oncolytic measles viruses displaying a single-chain antibody against CD38, a myeloma cell marker", Blood, 2003, vol. 101, No. 7, pp. 2557-2562.
Russell et al., "Oncolytic Virotherapy", Nat. Biotechnol., 2014, 30(7): 658-670.
Ungerechts et al., "Lymphoma Chemovirotherapy: CD20-Target and Convertase-Armed Measles Virus Can Synergize with Fludarabine", Cancer Res., 2007, 67(22), pp. 10939-10947.
Vongpunsawad et al., "Selectively Receptor-Blind Measles Viruses: Identification of Residues Necessary for SLAM- or CD46-Induced Fusion and Their Localization on a New Hemagglutinin Structural Model", J. Virol. 2004, vol. 78, No. 1, pp. 302-313.
Zaoui et al., "Chemovirotherapy for head and neck squamous cell carcinoma with EGFR-targeted and CD/UPRT-armed oncolytic measles virus", Cancer Gene Therapy, 2012, 19, pp. 181-191.
Blechacz et al., "Engineered Measles Virus as a Novel Oncolytic Viral Therapy System for Hepatocellular Carcinoma," Hepatology, 2006, vol. 44, No. 6, pp. 1465-1474.
Hu et al., "Using a HPV E7-Expressing Recombinant Measles Virus for Cervical Cancer Therapy," Abstracts of the Interscience Conference on Antimicrobial Agents and Chemotherapy, 2009, vol. 49, pp. 221-222, G1-881.

* cited by examiner

SEQUENCE LISTING

<160> NUMBER OF SEQ ID NOS: 5

<210> SEQ ID NO 1
<211> LENGTH: 1473
<212> TYPE: DNA
<213> ORGANISM: Homo sapiens

<400> SEQUENCE: 1

```
atgacggtgg acagcctagt gaacaaggag tgctgcccac gcctgggtgc agagtcggcc     60
aatgtctgtg gctctcagca aggccggggg cagtgcacag aggtgcgagc cgacacaagg    120
ccctggagtg gtccctacat cctacgaaac caggatgacc gtgagctgtg gccaagaaaa    180
ttcttccacc ggacctgcaa gtgcacagga aactttgccg gctataattg tggagactgc    240
aagtttggct ggaccggtcc caactgcgag cggaagaaac caccagtgat tcggcagaac    300
atccattcct tgagtcctca ggaaagagag cagttcttgg gcgccttaga tctcgcgaag    360
aagagagtac accccgacta cgtgatcacc acacaacact ggctgggcct gcttgggccc    420
aatggaaccc agccgcagtt tgccaactgc agtgtttatg atttttttgt gtggctccat    480
tattattctg ttagagatac attattagga ccaggacgcc cctacagggc catagatttc    540
tcacatcaag gacctgcatt tgttacctgg caccggtacc atttgttgtg tctggaaaga    600
gatctccagc gactcattgg caatgagtct tttgctttgc cctactggaa ctttgccact    660
gggaggaacg agtgtgatgt gtgtacagac cagctgtttg gggcagcgag accagacgat    720
ccgactctga ttagtcggaa ctcaagattc tccagctggg aaactgtctg tgatagcttg    780
gatgactaca accacctggt caccttgtgc aatggaacct atgaaggttt gctgagaaga    840
aatcaaatgg gaagaaacag catgaaattg ccaaccttaa aagacatacg agattgcctg    900
tctctccaga agtttgacaa tcctcccttc ttccagaact ctaccttcag tttcaggaat    960
gctttggaag ggtttgataa agcagatggg actctggatt ctcaagtgat gagccttcat   1020
aatttggttc attccttcct gaacgggaca aacgctttgc cacattcagc cgccaatgat   1080
cccatttttg tggttcttca ttcctttact gatgccatct ttgatgagtg gatgaaaaga   1140
tttaatcctc ctgcagatgc ctggcctcag gagctggccc ctattggtca caatcggatg   1200
tacaacatgg ttcctttctt ccctccagtg actaatgaag aactcttttt aacctcagac   1260
caacttggct acagctatgc catcgatctg ccagtttcag ttgaagaaac tccaggttgg   1320
cccacaactc tcttagtagt catgggaaca ctggtggctt tggttggtct ttttgtgctg   1380
ttggcttttc ttcaatatag aagacttcga aaaggatata cacccctaat ggagacacat   1440
ttaagcagca agagatacac agaagaagcc tag                                1473
```

<210> SEQ ID NO 2
<211> LENGTH: 490
<212> TYPE: PRT
<213> ORGANISM: Homo sapiens

<400> SEQUENCE: 2

-continued

```
Met Thr Val Asp Ser Leu Val Asn Lys Glu Cys Cys Pro Arg Leu Gly
1               5                   10                  15

Ala Glu Ser Ala Asn Val Cys Gly Ser Gln Gln Gly Arg Gly Gln Cys
            20                  25                  30

Thr Glu Val Arg Ala Asp Thr Arg Pro Trp Ser Gly Pro Tyr Ile Leu
        35                  40                  45

Arg Asn Gln Asp Asp Arg Glu Leu Trp Pro Arg Lys Phe Phe His Arg
    50                  55                  60

Thr Cys Lys Cys Thr Gly Asn Phe Ala Gly Tyr Asn Cys Gly Asp Cys
65                  70                  75                  80

Lys Phe Gly Trp Thr Gly Pro Asn Cys Glu Arg Lys Lys Pro Pro Val
                85                  90                  95

Ile Arg Gln Asn Ile His Ser Leu Ser Pro Gln Glu Arg Glu Gln Phe
            100                 105                 110

Leu Gly Ala Leu Asp Leu Ala Lys Lys Arg Val His Pro Asp Tyr Val
        115                 120                 125

Ile Thr Thr Gln His Trp Leu Gly Leu Leu Gly Pro Asn Gly Thr Gln
    130                 135                 140

Pro Gln Phe Ala Asn Cys Ser Val Tyr Asp Phe Phe Val Trp Leu His
145                 150                 155                 160

Tyr Tyr Ser Val Arg Asp Thr Leu Leu Gly Pro Gly Arg Pro Tyr Arg
                165                 170                 175

Ala Ile Asp Phe Ser His Gln Gly Pro Ala Phe Val Thr Trp His Arg
            180                 185                 190

Tyr His Leu Leu Cys Leu Glu Arg Asp Leu Gln Arg Leu Ile Gly Asn
        195                 200                 205

Glu Ser Phe Ala Leu Pro Tyr Trp Asn Phe Ala Thr Gly Arg Asn Glu
    210                 215                 220

Cys Asp Val Cys Thr Asp Gln Leu Phe Gly Ala Ala Arg Pro Asp Asp
225                 230                 235                 240

Pro Thr Leu Ile Ser Arg Asn Ser Arg Phe Ser Ser Trp Glu Thr Val
                245                 250                 255

Cys Asp Ser Leu Asp Asp Tyr Asn His Leu Val Thr Leu Cys Asn Gly
            260                 265                 270

Thr Tyr Glu Gly Leu Leu Arg Arg Asn Gln Met Gly Arg Asn Ser Met
        275                 280                 285

Lys Leu Pro Thr Leu Lys Asp Ile Arg Asp Cys Leu Ser Leu Gln Lys
    290                 295                 300

Phe Asp Asn Pro Pro Phe Phe Gln Asn Ser Thr Phe Ser Phe Arg Asn
305                 310                 315                 320

Ala Leu Glu Gly Phe Asp Lys Ala Asp Gly Thr Leu Asp Ser Gln Val
                325                 330                 335

Met Ser Leu His Asn Leu Val His Ser Phe Leu Asn Gly Thr Asn Ala
            340                 345                 350

Leu Pro His Ser Ala Ala Asn Asp Pro Ile Phe Val Val Leu His Ser
        355                 360                 365

Phe Thr Asp Ala Ile Phe Asp Glu Trp Met Lys Arg Phe Asn Pro Pro
    370                 375                 380

Ala Asp Ala Trp Pro Gln Glu Leu Ala Pro Ile Gly His Asn Arg Met
385                 390                 395                 400

Tyr Asn Met Val Pro Phe Phe Pro Pro Val Thr Asn Glu Glu Leu Phe
                405                 410                 415

Leu Thr Ser Asp Gln Leu Gly Tyr Ser Tyr Ala Ile Asp Leu Pro Val
```

```
            420                 425                 430

Ser Val Glu Glu Thr Pro Gly Trp Pro Thr Thr Leu Leu Val Val Met
        435                 440                 445

Gly Thr Leu Val Ala Leu Val Gly Leu Phe Val Leu Leu Ala Phe Leu
    450                 455                 460

Gln Tyr Arg Arg Leu Arg Lys Gly Tyr Thr Pro Leu Met Glu Thr His
465                 470                 475                 480

Leu Ser Ser Lys Arg Tyr Thr Glu Glu Ala
                485                 490


<210> SEQ ID NO 3
<211> LENGTH: 17448
<212> TYPE: DNA
<213> ORGANISM: Artificial
<220> FEATURE:
<223> OTHER INFORMATION: MeVac with natural tropism, encoding DCT in ATU
      downstream of H
<220> FEATURE:
<221> NAME/KEY: MeV leader
<222> LOCATION: (1)..(55)
<220> FEATURE:
<221> NAME/KEY: N ORF
<222> LOCATION: (108)..(1685)
<223> OTHER INFORMATION: (1578 nt = 525 aa +stop)
<220> FEATURE:
<221> NAME/KEY: P ORF
<222> LOCATION: (1807)..(3330)
<223> OTHER INFORMATION: (1524 nt = 507 aa +stop)
<220> FEATURE:
<221> NAME/KEY: V trans-frame
<222> LOCATION: (1807)..(2705)
<223> OTHER INFORMATION: (ORF after mRNA editing (non-structural; 900
      nt = 299 aa +stop)
<220> FEATURE:
<221> NAME/KEY: C ORF
<222> LOCATION: (1829)..(2389)
<223> OTHER INFORMATION: (non-structural; 561 nt = 186 aa +stop)
<220> FEATURE:
<221> NAME/KEY: M ORF
<222> LOCATION: (3438)..(4445)
<223> OTHER INFORMATION: (1008 nt = 335 aa +stop)
<220> FEATURE:
<221> NAME/KEY: F ORF (
<222> LOCATION: (5449)..(7110)
<223> OTHER INFORMATION: 1662 nt = 553 aa + stop)
<220> FEATURE:
<221> NAME/KEY: H ORF
<222> LOCATION: (7271)..(9124)
<223> OTHER INFORMATION: (1854 nt = 617 aa +stop)
<220> FEATURE:
<221> NAME/KEY: 5'-cloning site
<222> LOCATION: (9232)..(9238)
<223> OTHER INFORMATION: MauBI+MluI (CG'cgcgt)
<220> FEATURE:
<221> NAME/KEY: ORF human DCT
<222> LOCATION: (9245)..(10720)
<223> OTHER INFORMATION: (1476 nt = 490 aa +2 stop codons)
<220> FEATURE:
<221> NAME/KEY: 3'-cloning site
<222> LOCATION: (10720)..(10727)
<223> OTHER INFORMATION: AscI+MauBI (gg'CGCGCG)
<220> FEATURE:
<221> NAME/KEY: L ORF
<222> LOCATION: (10788)..(17339)
<223> OTHER INFORMATION: (6552 nt = 2183 aa +stop)
<220> FEATURE:
<221> NAME/KEY: MeV trailer
<222> LOCATION: (17412)..(17448)
<223> OTHER INFORMATION: (37 nt)

<400> SEQUENCE: 3

accaaacaaa gttgggtaag gatagttcaa tcaatgatca tcttctagtg cacttaggat     60
```

-continued

```
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
```

-continued

```
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
```

-continued

```
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac ggggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag gggggcgttgt  7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
```

-continued

```
tatctccggc ttccctctgg ccgaacaata tcggtagtta atcaaaactt agggtgcaag   7260
atcatccaca atgtcaccac aacgagaccg gataaatgcc ttctacaaag ataaccccca   7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatgggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcattttct tacttttatc cttttaggtt   8940
gcctataaag gggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
catccatcat tgttataaaa aacttaggaa ccaggtccac acagctcgag tcgcgcgtgc   9240
caccatgacg gtggacagcc tagtgaacaa ggagtgctgc ccacgcctgg gtgcagagtc   9300
ggccaatgtc tgtggctctc agcaaggccg gggggcagtgc acagaggtgc gagccgacac   9360
aaggccctgg agtggtccct acatcctacg aaaccaggat gaccgtgagc tgtggccaag   9420
aaaattcttc caccggacct gcaagtgcac aggaaacttt gccggctata attgtggaga   9480
ctgcaagttt ggctggaccg gtcccaactg cgagcggaag aaaccaccag tgattcggca   9540
```

-continued

```
gaacatccat tccttgagtc ctcaggaaag agagcagttc ttgggcgcct tagatctcgc   9600
gaagaagaga gtacaccccg actacgtgat caccacacaa cactggctgg gcctgcttgg   9660
gcccaatgga acccagccgc agtttgccaa ctgcagtgtt tatgattttt ttgtgtggct   9720
ccattattat tctgttagag atacattatt aggaccagga cgcccctaca gggccataga   9780
tttctcacat caaggacctg catttgttac ctggcaccgg taccatttgt tgtgtctgga   9840
aagagatctc cagcgactca ttggcaatga gtcttttgct ttgccctact ggaactttgc   9900
cactgggagg aacgagtgtg atgtgtgtac agaccagctg tttggggcag cgagaccaga   9960
cgatccgact ctgattagtc ggaactcaag attctccagc tgggaaactg tctgtgatag  10020
cttggatgac tacaaccacc tggtcacctt gtgcaatgga acctatgaag gtttgctgag  10080
aagaaatcaa atgggaagaa acagcatgaa attgccaacc ttaaaagaca tacgagattg  10140
cctgtctctc cagaagtttg acaatcctcc cttcttccag aactctacct tcagtttcag  10200
gaatgctttg gaagggtttg ataaagcaga tgggactctg gattctcaag tgatgagcct  10260
tcataatttg gttcattcct tcctgaacgg gacaaacgct ttgccacatt cagccgccaa  10320
tgatcccatt tttgtggttc ttcattcctt tactgatgcc atctttgatg agtggatgaa  10380
aagatttaat cctcctgcag atgcctggcc tcaggagctg gcccctattg gtcacaatcg  10440
gatgtacaac atggttcctt tcttccctcc agtgactaat gaagaactct tttaacctc   10500
agaccaactt ggctacagct atgccatcga tctgccagtt tcagttgaag aaactccagg  10560
ttggcccaca actctcttag tagtcatggg aacactggtg gctttggttg gtctttttgt  10620
gctgttggct tttcttcaat atagaagact tcgaaaagga tatacacccc taatggagac  10680
acatttaagc agcaagagat acacagaaga agcctagtag gcgcgcgttc tagtgtgaaa  10740
tagacatcag aattaagaaa aacgtagggt ccaagtggtt ccccgttatg gactcgctat  10800
ctgtcaacca gatcttatac cctgaagttc acctagatag cccgatagtt accaataaga  10860
tagtagccat cctggagtat gctcgagtcc ctcacgctta cagcctggag gaccctacac  10920
tgtgtcagaa catcaagcac cgcctaaaaa acggattttc caaccaaatg attataaaca  10980
atgtggaagt tgggaatgtc atcaagtcca agcttaggag ttatccggcc cactctcata  11040
ttccatatcc aaattgtaat caggatttat ttaacataga agacaaagag tcaacgagga  11100
agatccgtga actcctcaaa aaggggaatt cgctgtactc caaagtcagt gataaggttt  11160
tccaatgctt aagggacact aactcacggc ttggcctagg ctccgaattg agggaggaca  11220
tcaaggagaa agttattaac ttgggagttt acatgcacag ctcccagtgg tttgagccct  11280
ttctgttttg gtttacagtc aagactgaga tgaggtcagt gattaaatca caaacccata  11340
cttgccatag gaggagacac acacctgtat tcttcactgg tagttcagtt gagttgctaa  11400
tctctcgtga ccttgttgct ataatcagta aagagtctca acatgtatat tacctgacat  11460
ttgaactggt tttgatgtat tgtgatgtca tagaggggag gttaatgaca gagaccgcta  11520
tgactattga tgctaggtat acagagcttc taggaagagt cagatacatg tggaaactga  11580
tagatggttt cttccctgca ctcgggaatc caacttatca aattgtagcc atgctggagc  11640
ctctttcact tgcttacctg cagctgaggg atataacagt agaactcaga ggtgctttcc  11700
ttaaccactg ctttactgaa atacatgatg ttcttgacca aaacgggttt tctgatgaag  11760
gtacttatca tgagttaact gaagctctag attacatttt cataactgat gacatacatc  11820
tgacagggga gattttctca tttttcagaa gtttcggcca ccccagactt gaagcagtaa  11880
cggctgctga aaatgttagg aaatacatga atcagcctaa agtcattgtg tatgagactc  11940
```

-continued

```
tgatgaaagg tcatgccata ttttgtggaa tcataatcaa cggctatcgt gacaggcacg  12000
gaggcagttg gccaccgctg accctccccc tgcatgctgc agacacaatc cggaatgctc  12060
aagcttcagg tgaagggtta acacatgagc agtgcgttga taactggaaa tcttttgctg  12120
gagtgaaatt tggctgcttt atgcctctta gcctggatag tgatctgaca atgtacctaa  12180
aggacaaggc acttgctgct ctccaaaggg aatgggattc agtttacccg aaagagttcc  12240
tgcgttacga ccctcccaag ggaaccgggt cacggaggct tgtagatgtt ttccttaatg  12300
attcgagctt tgacccatat gatgtgataa tgtatgttgt aagtggagct tacctccatg  12360
accctgagtt caacctgtct tacagcctga aagaaaagga gatcaaggaa acaggtagac  12420
tttttgctaa aatgacttac aaaatgaggg catgccaagt gattgctgaa aatctaatct  12480
caaacgggat tggcaaatat tttaaggaca atgggatggc caaggatgag cacgatttga  12540
ctaaggcact ccacactcta gctgtctcag gagtccccaa agatctcaaa gaaagtcaca  12600
ggggggggcc agtcttaaaa acctactccc gaagcccagt ccacacaagt accaggaacg  12660
tgagagcagc aaaagggttt atagggttcc ctcaagtaat tcggcaggac caagacactg  12720
atcatccgga gaatatggaa gcttacgaga cagtcagtgc atttatcacg actgatctca  12780
agaagtactg ccttaattgg agatatgaga ccatcagctt gtttgcacag aggctaaatg  12840
agatttacgg attgccctca tttttccagt ggctgcataa gaggcttgag acctctgtcc  12900
tgtatgtaag tgaccctcat tgcccccccg accttgacgc ccatatcccg ttatataaag  12960
tccccaatga tcaaatcttc attaagtacc ctatgggagg tatagaaggg tattgtcaga  13020
agctgtggac catcagcacc attccctatc tatacctggc tgcttatgag agcggagtaa  13080
ggattgcttc gttagtgcaa ggggacaatc agaccatagc cgtaacaaaa agggtaccca  13140
gcacatggcc ctacaacctt aagaaacggg aagctgctag agtaactaga gattactttg  13200
taattcttag gcaaaggcta catgatattg gccatcacct caaggcaaat gagacaattg  13260
tttcatcaca ttttttgtc tattcaaaag gaatatatta tgatgggcta cttgtgtccc  13320
aatcactcaa gagcatcgca agatgtgtat tctggtcaga gactatagtt gatgaaacaa  13380
gggcagcatg cagtaatatt gctacaacaa tggctaaaag catcgagaga ggttatgacc  13440
gttaccttgc atattccctg aacgtcctaa aagtgataca gcaaattctg atctctcttg  13500
gcttcacaat caattcaacc atgacccggg atgtagtcat acccctcctc acaaacaacg  13560
acctcttaat aaggatggca ctgttgcccg ctcctattgg ggggatgaat tatctgaata  13620
tgagcaggct gtttgtcaga aacatcggtg atccagtaac atcatcaatt gctgatctca  13680
agagaatgat tctcgcctca ctaatgcctg aagagaccct ccatcaagta atgacacaac  13740
aaccggggga ctcttcattc ctagactggg ctagcgaccc ttactcagca aatcttgtat  13800
gtgtccagag catcactaga ctcctcaaga acataactgc aaggtttgtc ctgatccata  13860
gtccaaaccc aatgttaaaa ggattattcc atgatgacag taaagaagag gacgagggac  13920
tggcggcatt cctcatggac aggcatatta tagtacctag ggcagctcat gaaatcctgg  13980
atcatagtgt cacaggggca agagagtcta ttgcaggcat gctggatacc acaaaaggct  14040
tgattcgagc cagcatgagg aagggggggt taacctctcg agtgataacc agattgtcca  14100
attatgacta tgaacaattc agagcaggga tggtgctatt gacaggaaga aagagaaatg  14160
tcctcattga caaagagtca tgttcagtgc agctggcgag agctctaaga agccatatgt  14220
gggcgaggct agctcgagga cggcctattt acggccttga ggtccctgat gtactagaat  14280
```

-continued

```
ctatgcgagg ccaccttatt cggcgtcatg agacatgtgt catctgcgag tgtggatcag  14340
tcaactacgg atggtttttt gtcccctcgg gttgccaact ggatgatatt gacaaggaaa  14400
catcatcctt gagagtccca tatattggtt ctaccactga tgagagaaca gacatgaagc  14460
ttgccttcgt aagagcccca agtcgatcct tgcgatctgc tgttagaata gcaacagtgt  14520
actcatgggc ttacggtgat gatgatagct cttggaacga agcctggttg ttggctaggc  14580
aaagggccaa tgtgagcctg gaggagctaa gggtgatcac tcccatctca acttcgacta  14640
atttagcgca taggttgagg gatcgtagca ctcaagtgaa atactcaggt acatcccttg  14700
tccgagtggc gaggtatacc acaatctcca acgacaatct ctcatttgtc atatcagata  14760
agaaggttga tactaacttt atataccaac aaggaatgct tctagggttg ggtgttttag  14820
aaacattgtt tcgactcgag aaagataccg gatcatctaa cacggtatta catcttcacg  14880
tcgaaacaga ttgttgcgtg atcccgatga tagatcatcc caggataccc agctcccgca  14940
agctagagct gagggcagag ctatgtacca acccattgat atatgataat gcacctttaa  15000
ttgacagaga tgcaacaagg ctatacaccc agagccatag gaggcacctt gtggaatttg  15060
ttacatggtc cacaccccaa ctatatcaca ttttagctaa gtccacagca ctatctatga  15120
ttgacctggt aacaaaattt gagaaggacc atatgaatga aatttcagct ctcatagggg  15180
atgacgatat caatagtttc ataactgagt ttctgctcat agagccaaga ttattcacta  15240
tctacttggg ccagtgtgcg gccatcaatt gggcatttga tgtacattat catagaccat  15300
cagggaaata tcagatgggt gagctgttgt catcgttcct ttctagaatg agcaaaggag  15360
tgtttaaggt gcttgtcaat gctctaagcc acccaaagat ctacaagaaa ttctggcatt  15420
gtggtattat agagcctatc catggtcctt cacttgatgc tcaaaacttg cacacaactg  15480
tgtgcaacat ggtttacaca tgctatatga cctacctcga cctgttgttg aatgaagagt  15540
tagaagagtt cacatttctc ttgtgtgaaa gcgacgagga tgtagtaccg gacagattcg  15600
acaacatcca ggcaaaacac ttatgtgttc tggcagattt gtactgtcaa ccagggacct  15660
gcccaccaat tcgaggtcta agaccggtag agaaatgtgc agttctaacc gaccatatca  15720
aggcagaggc tatgttatct ccagcaggat cttcgtggaa cataaatcca attattgtag  15780
accattactc atgctctctg acttatctcc ggcgaggatc gatcaaacag ataagattga  15840
gagttgatcc aggattcatt ttcgacgccc tcgctgaggt aaatgtcagt cagccaaaga  15900
tcggcagcaa caacatctca aatatgagca tcaaggcttt cagacccccc cacgatgatg  15960
ttgcaaaatt gctcaaagat atcaacacaa gcaagcacaa tcttcccatt tcagggggca  16020
atctcgccaa ttatgaaatc catgctttcc gcagaatcgg gttgaactca tctgcttgct  16080
acaaagctgt tgagatatca acattaatta ggagatgcct tgagccaggg gaggacggct  16140
tgttcttggg tgagggatcg ggttctatgt tgatcactta taaagagata cttaaactaa  16200
acaagtgctt ctataatagt ggggtttccg ccaattctag atctggtcaa agggaattag  16260
caccctatcc ctccgaagtt ggccttgtcg aacacagaat gggagtaggt aatattgtca  16320
aagtgctctt taacgggagg cccgaagtca cgtgggtagg cagtgtagat tgcttcaatt  16380
tcatagttag taatatccct acctctagtg tggggtttat ccattcagat atagagacct  16440
tgcctgacaa agatactata gagaagctag aggaattggc agccatctta tcgatggctc  16500
tgctcctggg caaaatagga tcaatactgg tgattaagct tatgcctttc agcggggatt  16560
ttgttcaggg atttataagt tatgtagggt ctcattatag agaagtgaac cttgtatacc  16620
ctagatacag caacttcatc tctactgaat cttatttggt tatgacagat ctcaaggcta  16680
```

-continued

```
accggctaat gaatcctgaa aagattaagc agcagataat tgaatcatct gtgaggactt  16740

cacctggact tataggtcac atcctatcca ttaagcaact aagctgcata caagcaattg  16800

tgggagacgc agttagtaga ggtgatatca atcctactct gaaaaaactt acacctatag  16860

agcaggtgct gatcaattgc gggttggcaa ttaacggacc taagctgtgc aaagaattga  16920

tccaccatga tgttgcctca gggcaagatg gattgcttaa ttctatactc atcctctaca  16980

gggagttggc aagattcaaa gacaaccaaa gaagtcaaca agggatgttc cacgcttacc  17040

ccgtattggt aagtagcagg caacgagaac ttatatctag gatcacccgc aaattctggg  17100

ggcacattct tctttactcc gggaacaaaa agttgataaa taagtttatc cagaatctca  17160

agtccggcta tctgatacta gacttacacc agaatatctt cgttaagaat ctatccaagt  17220

cagagaaaca gattattatg acggggggtt tgaaacgtga gtgggttttt aaggtaacag  17280

tcaaggagac caaagaatgg tataagttag tcggatacag tgccctgatt aaggactaat  17340

tggttgaact ccggaaccct aatcctgccc taggtggtta ggcattattt gcaatatatt  17400

aaagaaaact ttgaaaatac gaagtttcta ttcccagctt tgtctggt              17448
```

<210> SEQ ID NO 4
<211> LENGTH: 18258
<212> TYPE: DNA
<213> ORGANISM: Artificial
<220> FEATURE:
<223> OTHER INFORMATION: MeVac retargeted to human CD20, encoding DCT in ATU downstream of HaCD20
<220> FEATURE:
<221> NAME/KEY: MeV leader
<222> LOCATION: (1)..(55)
<220> FEATURE:
<221> NAME/KEY: N ORF
<222> LOCATION: (108)..(1685)
<223> OTHER INFORMATION: (1578 nt = 525 aa +stop)
<220> FEATURE:
<221> NAME/KEY: P ORF
<222> LOCATION: (1807)..(3330)
<223> OTHER INFORMATION: (1524 nt = 507 aa +stop)
<220> FEATURE:
<221> NAME/KEY: V trans-frame
<222> LOCATION: (1807)..(2705)
<223> OTHER INFORMATION: (ORF after mRNA editing (non-structural; 900 nt = 299 aa +stop)
<220> FEATURE:
<221> NAME/KEY: C ORF
<222> LOCATION: (1829)..(2389)
<223> OTHER INFORMATION: (non-structural; 561 nt = 186 aa +stop)
<220> FEATURE:
<221> NAME/KEY: M ORF
<222> LOCATION: (3438)..(4445)
<223> OTHER INFORMATION: (1008 nt = 335 aa +stop)
<220> FEATURE:
<221> NAME/KEY: F ORF
<222> LOCATION: (5449)..(7110)
<223> OTHER INFORMATION: (1662 nt = 553 aa + stop)
<220> FEATURE:
<221> NAME/KEY: HaCD20 ORF
<222> LOCATION: (7271)..(9934)
<223> OTHER INFORMATION: (2664 nt = 886 aa +2 stop codons)
<220> FEATURE:
<221> NAME/KEY: ORF human DCT
<222> LOCATION: (10055)..(11530)
<223> OTHER INFORMATION: (1476 nt = 490 aa +2 stop codons)
<220> FEATURE:
<221> NAME/KEY: L ORF
<222> LOCATION: (11598)..(18149)
<223> OTHER INFORMATION: (6552 nt = 2183 aa +stop)
<220> FEATURE:
<221> NAME/KEY: MeV trailer
<222> LOCATION: (18222)..(18258)
<223> OTHER INFORMATION: (37 nt)

-continued

<400> SEQUENCE: 4

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggcca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
```

-continued

```
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
```

```
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac ggggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag ggggcgttgt   7020
```

-continued

```
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataacccca    7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc gcactcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgttttggc aacctacgat acttccgcgg ttgaacatgc   8880
tgtggtttat tacgtttaca gcccaagccg cctatcgtct tacttttatc cttttaggtt   8940
gcctataaag gggtccccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatgcggc   9120
ccagccggcc atcgagggaa ggatggctca ggttcagctg gtccagtcag ggctgagct    9180
ggtgaagcct ggggcctcag tgaagatgtc ctgcaaggct tctggctaca catttaccag   9240
ttacaatatg cactgggtaa agcagacacc tggacagggc ctggaatgga ttggagctat   9300
ttatccagga aatggtgata cttcctacaa tcagaagttc aaaggcaagg ccacattgac   9360
tgcagacaaa tcctccagca cagcctacat gcagctcagc agcctgacat ctgaggactc   9420
```

-continued

```
tgcggtctat tactgtgcaa gagcgcaatt acgacctaac tactggtact tcgatgtctg   9480
gggcgcaggg accacggtca ccgtgagcaa gatctctggt ggcggtggct cgggcggtgg   9540
tgggtcgggt ggcggaggct cgggtggctc gagcgacatc gtgctgtcgc agtctccagc   9600
aatcctgtct gcatctccag gggagaaggt cacaatgact tgcagggcca gctcaagtgt   9660
aagttacatg cactggtacc agcagaagcc aggatcctcc cccaaaccct ggatttatgc   9720
cacatccaac ctggcttctg gagtccctgc tcgcttcagt ggcagtgggt ctgggacctc   9780
ttactctctc acaatcagca gagtggaggc tgaagatgct gccacttatt actgccagca   9840
gtggattagt aacccaccca cgttcggtgc tgggaccaag ctggagctga aggcggccgc   9900
aagaggttct catcaccatc accatcacta atagggctgc tagtgaacca atcacatgat   9960
gtcacccaga catcaggcat acccactagt catccatcat tgttataaaa aacttaggaa  10020
ccaggtccac acagctcgag tcgcgcgtgc caccatgacg gtggacagcc tagtgaacaa  10080
ggagtgctgc ccacgcctgg gtgcagagtc ggccaatgtc tgtggctctc agcaaggccg  10140
ggggcagtgc acagaggtgc gagccgacac aaggccctgg agtggtccct acatcctacg  10200
aaaccaggat gaccgtgagc tgtggccaag aaaattcttc caccggacct gcaagtgcac  10260
aggaaacttt gccggctata attgtggaga ctgcaagttt ggctggaccg gtcccaactg  10320
cgagcggaag aaaccaccag tgattcggca gaacatccat tccttgagtc ctcaggaaag  10380
agagcagttc ttgggcgcct tagatctcgc gaagaagaga gtacaccccg actacgtgat  10440
caccacacaa cactggctgg gcctgcttgg gcccaatgga acccagccgc agtttgccaa  10500
ctgcagtgtt tatgattttt ttgtgtggct ccattattat tctgttagag atacattatt  10560
aggaccagga cgcccctaca gggccataga tttctcacat caaggacctg catttgttac  10620
ctggcaccgg taccatttgt tgtgtctgga aagagatctc cagcgactca ttggcaatga  10680
gtcttttgct ttgccctact ggaactttgc cactgggagg aacgagtgtg atgtgtgtac  10740
agaccagctg tttggggcag cgagaccaga cgatccgact ctgattagtc ggaactcaag  10800
attctccagc tgggaaactg tctgtgatag cttggatgac tacaaccacc tggtcacctt  10860
gtgcaatgga acctatgaag gtttgctgag aagaaatcaa atgggaagaa acagcatgaa  10920
attgccaacc ttaaaagaca tacgagattg cctgtctctc cagaagtttg acaatcctcc  10980
cttcttccag aactctacct tcagtttcag gaatgctttg gaagggtttg ataaagcaga  11040
tgggactctg gattctcaag tgatgagcct tcataatttg gttcattcct tcctgaacgg  11100
gacaaacgct ttgccacatt cagccgccaa tgatcccatt tttgtggttc ttcattcctt  11160
tactgatgcc atctttgatg agtggatgaa aagatttaat cctcctgcag atgcctggcc  11220
tcaggagctg gcccctattg gtcacaatcg gatgtacaac atggttcctt tcttccctcc  11280
agtgactaat gaagaactct ttttaacctc agaccaactt ggctacagct atgccatcga  11340
tctgccagtt tcagttgaag aaactccagg ttggcccaca actctcttag tagtcatggg  11400
aacactggtg gctttggttg gtctttttgt gctgttggct tttcttcaat atagaagact  11460
tcgaaaagga tatacacccc taatggagac acatttaagc agcaagagat acacagaaga  11520
agcctagtag gcgcgcgttc tagtgtgaaa tagacatcag aattaagaaa aacgtagggt  11580
ccaagtggtt ccccgttatg gactcgctat ctgtcaacca gatcttatac cctgaagttc  11640
acctagatag cccgatagtt accaataaga tagtagccat cctggagtat gctcgagtcc  11700
ctcacgctta cagcctggag gaccctacac tgtgtcagaa catcaagcac cgcctaaaaa  11760
```

```
acggattttc caaccaaatg attataaaca atgtggaagt tgggaatgtc atcaagtcca  11820
agcttaggag ttatccggcc cactctcata ttccatatcc aaattgtaat caggatttat  11880
ttaacataga agacaaagag tcaacgagga agatccgtga actcctcaaa aaggggaatt  11940
cgctgtactc caaagtcagt gataaggttt tccaatgctt aagggacact aactcacggc  12000
ttggcctagg ctccgaattg agggaggaca tcaaggagaa agttattaac ttgggagttt  12060
acatgcacag ctcccagtgg tttgagccct ttctgttttg gtttacagtc aagactgaga  12120
tgaggtcagt gattaaatca caaacccata cttgccatag gaggagacac acacctgtat  12180
tcttcactgg tagttcagtt gagttgctaa tctctcgtga ccttgttgct ataatcagta  12240
aagagtctca acatgtatat tacctgacat ttgaactggt tttgatgtat tgtgatgtca  12300
tagaggggag gttaatgaca gagaccgcta tgactattga tgctaggtat acagagcttc  12360
taggaagagt cagatacatg tggaaactga tagatggttt cttccctgca ctcgggaatc  12420
caacttatca aattgtagcc atgctggagc ctctttcact tgcttacctg cagctgaggg  12480
atataacagt agaactcaga ggtgctttcc ttaaccactg ctttactgaa atacatgatg  12540
ttcttgacca aaacgggttt tctgatgaag gtacttatca tgagttaact gaagctctag  12600
attacatttt cataactgat gacatacatc tgacagggga gattttctca tttttcagaa  12660
gtttcggcca ccccagactt gaagcagtaa cggctgctga aaatgttagg aaatacatga  12720
atcagcctaa agtcattgtg tatgagactc tgatgaaagg tcatgccata ttttgtggaa  12780
tcataatcaa cggctatcgt gacaggcacg gaggcagttg gccaccgctg accctccccc  12840
tgcatgctgc agacacaatc cggaatgctc aagcttcagg tgaagggtta acacatgagc  12900
agtgcgttga taactggaaa tcttttgctg gagtgaaatt tggctgcttt atgcctctta  12960
gcctggatag tgatctgaca atgtacctaa aggacaaggc acttgctgct ctccaaaggg  13020
aatgggattc agtttacccg aaagagttcc tgcgttacga ccctcccaag ggaaccgggt  13080
cacggaggct tgtagatgtt ttccttaatg attcgagctt tgacccatat gatgtgataa  13140
tgtatgttgt aagtggagct tacctccatg accctgagtt caacctgtct tacagcctga  13200
aagaaaagga gatcaaggaa acaggtagac tttttgctaa aatgacttac aaaatgaggg  13260
catgccaagt gattgctgaa aatctaatct caaacgggat tggcaaatat tttaaggaca  13320
atgggatggc caaggatgag cacgatttga ctaaggcact ccacactcta gctgtctcag  13380
gagtccccaa agatctcaaa gaaagtcaca gggggggcc agtcttaaaa acctactccc  13440
gaagcccagt ccacacaagt accaggaacg tgagagcagc aaaagggttt atagggttcc  13500
ctcaagtaat tcggcaggac caagacactg atcatccgga gaatatggaa gcttacgaga  13560
cagtcagtgc atttatcacg actgatctca agaagtactg ccttaattgg agatatgaga  13620
ccatcagctt gtttgcacag aggctaaatg agatttacgg attgccctca tttttccagt  13680
ggctgcataa gaggcttgag acctctgtcc tgtatgtaag tgaccctcat tgcccccccg  13740
accttgacgc ccatatcccg ttatataaag tccccaatga tcaaatcttc attaagtacc  13800
ctatgggagg tatagaaggg tattgtcaga agctgtggac catcagcacc attccctatc  13860
tatacctggc tgcttatgag agcggagtaa ggattgcttc gttagtgcaa ggggacaatc  13920
agaccatagc cgtaacaaaa agggtaccca gcacatggcc ctacaacctt aagaaacggg  13980
aagctgctag agtaactaga gattactttg taattcttag gcaaaggcta catgatattg  14040
gccatcacct caaggcaaat gagacaattg tttcatcaca tttttttgtc tattcaaaag  14100
gaatatatta tgatgggcta cttgtgtccc aatcactcaa gagcatcgca agatgtgtat  14160
```

```
tctggtcaga gactatagtt gatgaaacaa gggcagcatg cagtaatatt gctacaacaa  14220
tggctaaaag catcgagaga ggttatgacc gttaccttgc atattccctg aacgtcctaa  14280
aagtgataca gcaaattctg atctctcttg gcttcacaat caattcaacc atgacccggg  14340
atgtagtcat acccctcctc acaaacaacg acctcttaat aaggatggca ctgttgcccg  14400
ctcctattgg ggggatgaat tatctgaata tgagcaggct gtttgtcaga aacatcggtg  14460
atccagtaac atcatcaatt gctgatctca agagaatgat tctcgcctca ctaatgcctg  14520
aagagaccct ccatcaagta atgacacaac aaccggggga ctcttcattc ctagactggg  14580
ctagcgaccc ttactcagca aatcttgtat gtgtccagag catcactaga ctcctcaaga  14640
acataactgc aaggtttgtc ctgatccata gtccaaaccc aatgttaaaa ggattattcc  14700
atgatgacag taaagaagag gacgagggac tggcggcatt cctcatggac aggcatatta  14760
tagtacctag ggcagctcat gaaatcctgg atcatagtgt cacaggggca agagagtcta  14820
ttgcaggcat gctggatacc acaaaaggct tgattcgagc cagcatgagg aagggggggt  14880
taacctctcg agtgataacc agattgtcca attatgacta tgaacaattc agagcaggga  14940
tggtgctatt gacaggaaga aagagaaatg tcctcattga caaagagtca tgttcagtgc  15000
agctggcgag agctctaaga agccatatgt gggcgaggct agctcgagga cggcctattt  15060
acggccttga ggtccctgat gtactagaat ctatgcgagg ccaccttatt cggcgtcatg  15120
agacatgtgt catctgcgag tgtggatcag tcaactacgg atggtttttt gtcccctcgg  15180
gttgccaact ggatgatatt gacaaggaaa catcatcctt gagagtccca tatattggtt  15240
ctaccactga tgagagaaca gacatgaagc ttgccttcgt aagagcccca agtcgatcct  15300
tgcgatctgc tgttagaata gcaacagtgt actcatgggc ttacggtgat gatgatagct  15360
cttggaacga agcctggttg ttggctaggc aaagggccaa tgtgagcctg gaggagctaa  15420
gggtgatcac tcccatctca acttcgacta atttagcgca taggttgagg gatcgtagca  15480
ctcaagtgaa atactcaggt acatcccttg tccgagtggc gaggtatacc acaatctcca  15540
acgacaatct ctcatttgtc atatcagata agaaggttga tactaacttt atataccaac  15600
aaggaatgct tctagggttg ggtgttttag aaacattgtt tcgactcgag aaagataccg  15660
gatcatctaa cacggtatta catcttcacg tcgaaacaga ttgttgcgtg atcccgatga  15720
tagatcatcc caggataccc agctcccgca agctagagct gagggcagag ctatgtacca  15780
acccattgat atatgataat gcacctttaa ttgacagaga tgcaacaagg ctatacaccc  15840
agagccatag gaggcacctt gtggaatttg ttacatggtc cacaccccaa ctatatcaca  15900
ttttagctaa gtccacagca ctatctatga ttgacctggt aacaaaattt gagaaggacc  15960
atatgaatga aatttcagct ctcatagggg atgacgatat caatagtttc ataactgagt  16020
ttctgctcat agagccaaga ttattcacta tctacttggg ccagtgtgcg gccatcaatt  16080
gggcatttga tgtacattat catagaccat cagggaaata tcagatgggt gagctgttgt  16140
catcgttcct ttctagaatg agcaaaggag tgtttaaggt gcttgtcaat gctctaagcc  16200
acccaaagat ctacaagaaa ttctggcatt gtggtattat agagcctatc catggtcctt  16260
cacttgatgc tcaaaacttg cacacaactg tgtgcaacat ggtttacaca tgctatatga  16320
cctacctcga cctgttgttg aatgaagagt tagaagagtt cacatttctc ttgtgtgaaa  16380
gcgacgagga tgtagtaccg gacagattcg acaacatcca ggcaaaacac ttatgtgttc  16440
tggcagattt gtactgtcaa ccagggacct gcccaccaat tcgaggtcta agaccggtag  16500
```

-continued agaaatgtgc agttctaacc gaccatatca aggcagaggc tatgttatct ccagcaggat 16560
cttcgtggaa cataaatcca attattgtag accattactc atgctctctg acttatctcc 16620
ggcgaggatc gatcaaacag ataagattga gagttgatcc aggattcatt ttcgacgccc 16680
tcgctgaggt aaatgtcagt cagccaaaga tcggcagcaa caacatctca aatatgagca 16740
tcaaggcttt cagacccccca cacgatgatg ttgcaaaatt gctcaaagat atcaacacaa 16800
gcaagcacaa tcttcccatt tcagggggca atctcgccaa ttatgaaatc catgctttcc 16860
gcagaatcgg gttgaactca tctgcttgct acaaagctgt tgagatatca acattaatta 16920
ggagatgcct tgagccaggg gaggacggct tgttcttggg tgagggatcg ggttctatgt 16980
tgatcactta taaagagata cttaaactaa acaagtgctt ctataatagt ggggtttccg 17040
ccaattctag atctggtcaa agggaattag caccctatcc ctccgaagtt ggccttgtcg 17100
aacacagaat gggagtaggt aatattgtca aagtgctctt taacgggagg cccgaagtca 17160
cgtgggtagg cagtgtagat tgcttcaatt tcatagttag taatatccct acctctagtg 17220
tggggtttat ccattcagat atagagacct tgcctgacaa agatactata gagaagctag 17280
aggaattggc agccatctta tcgatggctc tgctcctggg caaaatagga tcaatactgg 17340
tgattaagct tatgcctttc agcggggatt ttgttcaggg atttataagt tatgtagggt 17400
ctcattatag agaagtgaac cttgtatacc ctagatacag caacttcatc tctactgaat 17460
cttatttggt tatgacagat ctcaaggcta accggctaat gaatcctgaa aagattaagc 17520
agcagataat tgaatcatct gtgaggactt cacctggact tataggtcac atcctatcca 17580
ttaagcaact aagctgcata caagcaattg tgggagacgc agttagtaga ggtgatatca 17640
atcctactct gaaaaaactt acacctatag agcaggtgct gatcaattgc gggttggcaa 17700
ttaacggacc taagctgtgc aaagaattga tccaccatga tgttgcctca gggcaagatg 17760
gattgcttaa ttctatactc atcctctaca gggagttggc aagattcaaa gacaaccaaa 17820
gaagtcaaca agggatgttc cacgcttacc ccgtattggt aagtagcagg caacgagaac 17880
ttatatctag gatcacccgc aaattctggg ggcacattct tctttactcc gggaacaaaa 17940
agttgataaa taagtttatc cagaatctca agtccggcta tctgatacta gacttacacc 18000
agaatatctt cgttaagaat ctatccaagt cagagaaaca gattattatg acggggggtt 18060
tgaaacgtga gtgggttttt aaggtaacag tcaaggagac caaagaatgg tataagttag 18120
tcggatacag tgccctgatt aaggactaat tggttgaact ccggaaccct aatcctgccc 18180
taggtggtta ggcattattt gcaatatatt aaagaaaact ttgaaaatac gaagtttcta 18240
ttcccagctt tgtctggt 18258

<210> SEQ ID NO 5
<211> LENGTH: 18240
<212> TYPE: DNA
<213> ORGANISM: Artificial
<220> FEATURE:
<223> OTHER INFORMATION: MeVac retargeted to human CEA, encoding DCT in
ATU downstream of HaCEA
<220> FEATURE:
<221> NAME/KEY: MeV leader
<222> LOCATION: (1)..(55)
<220> FEATURE:
<221> NAME/KEY: N ORF
<222> LOCATION: (108)..(1685)
<223> OTHER INFORMATION: (1578 nt = 525 aa +stop)
<220> FEATURE:
<221> NAME/KEY: P ORF
<222> LOCATION: (1807)..(3330)
<223> OTHER INFORMATION: (1524 nt = 507 aa +stop)

-continued

<220> FEATURE:
<221> NAME/KEY: V trans-frame
<222> LOCATION: (1807)..(2705)
<223> OTHER INFORMATION: (ORF after mRNA editing (non-structural; 900
      nt = 299 aa +stop)
<220> FEATURE:
<221> NAME/KEY: C ORF
<222> LOCATION: (1829)..(2389)
<223> OTHER INFORMATION: (non-structural; 561 nt = 186 aa +stop)
<220> FEATURE:
<221> NAME/KEY: M ORF
<222> LOCATION: (3438)..(4445)
<223> OTHER INFORMATION: (1008 nt = 335 aa +stop)
<220> FEATURE:
<221> NAME/KEY: F ORF
<222> LOCATION: (5449)..(7110)
<223> OTHER INFORMATION: (1662 nt = 553 aa + stop)
<220> FEATURE:
<221> NAME/KEY: HaCEA ORF
<222> LOCATION: (7271)..(9916)
<223> OTHER INFORMATION: (2646 nt = 880 aa +2 stop codons)
<220> FEATURE:
<221> NAME/KEY: ORF human DCT
<222> LOCATION: (10037)..(11512)
<223> OTHER INFORMATION: (1476 nt = 490 aa +2 stop codons)
<220> FEATURE:
<221> NAME/KEY: L ORF
<222> LOCATION: (11580)..(18131)
<223> OTHER INFORMATION: (6552 nt = 2183 aa +stop)
<220> FEATURE:
<221> NAME/KEY: MeV trailer
<222> LOCATION: (18204)..(18240)
<223> OTHER INFORMATION: (37 nt)

<400> SEQUENCE: 5
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcgg gaacaaggaa atctcagata ttgaagtgca agaccctgag ggattcaaca 600
tgattctggg taccatccta gcccaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020 aaatgggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200
ggcaagagat ggtaaggagg tcagctggaa aggtcagttc cacattggca tctgaactcg 1260
gtatcactgc cgaggatgca aggcttgttt cagagattgc aatgcatact actgaggaca 1320

```
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tggggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
```

-continued

```
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac gggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
```

```
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag ggggcgttgt   7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataacccca    7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
```

-continued aatggagaca tgcttccaac aggcgtgtaa gggtaaaatc caagcactct gcgagaatcc 8460
cgagtgggca ccattgaagg ataacaggat tccttcatac ggggtcttgt ctgttgatct 8520
gagtctgaca gttgagctta aatcaaaat tgcttcggga ttcgggccat tgatcacaca 8580
cggttcaggg atggacctat acaaatccaa ccacaacaat gtgtattggc tgactatccc 8640
gccaatgaag aacctagcct taggtgtaat caacacattg gagtggatac cgagattcaa 8700
ggttagtccc gcactcttca ctgtcccaat taaggaagca ggcgaagact gccatgcccc 8760
aacataccta cctgcggagg tggatggtga tgtcaaactc agttccaatc tggtgattct 8820
acctggtcaa gatctccaat atgttttggc aacctacgat acttccgcgg ttgaacatgc 8880
tgtggtttat tacgtttaca gcccaagccg cctatcgtct tacttttatc cttttaggtt 8940
gcctataaag gggtccccca tcgaattaca agtggaatgc ttcacatggg accaaaaact 9000
ctggtgccgt cacttctgtg tgcttgcgga ctcagaatct ggtggacata tcactcactc 9060
tgggatggtg ggcatgggag tcagctgcac agtcacccgg gaagatggaa ccaatgcggc 9120
ccagccggcc atcgagggaa ggatggctca ggtgaaactg cagcagtctg gggcagaact 9180
tgtgaggtca gggacctcag tcaagttgtc ctgcacagct tctggcttca acattaaaga 9240
ctcctatatg cactggttga ggcaggggcc tgaacagtgc ctcgagtgga ttggatggat 9300
tgatcctgag aatggtgata ctgaatatgc cccgaagttc cagggcaagg ccacttttac 9360
tacagacaca tcctccaaca cagcctacct gcagctcagc agcctgacat ctgaggacac 9420
tgccgtctat tattgtaatg aggggactcc gactgggccg tactactttg actactgggg 9480
ccaagggacc acggtcaccg tctcctcagg tggaggcggt tcaggcggag gtggctctgg 9540
cggtggcgga tcagaaaatg tgctcaccca gtctccagca atcatgtctg catctccagg 9600
ggagaaggtc accataacct gcagtgccag ctcaagtgta agttacatgc actggttcca 9660
gcagaagcca ggcacttctc ccaaactctg gatttatagc acatccaacc tggcttctgg 9720
agtccctgct cgcttcagtg gcagtggatc tgggacctct tactctctca caatcagccg 9780
aatggaggct gaagatgctg ccacttatta ctgccagcaa aggagtagtt acccactcac 9840
gttcggttgt ggcaccaagc tcgagctgaa acgggcggcc gcaagaggtt ctcatcacca 9900
tcaccatcac taatagggct gctagtgaac caatcacatg atgtcaccca gacatcaggc 9960
atacccacta gtcatccatc attgttataa aaaacttagg aaccaggtcc acacagctcg 10020
agtcgcgcgt gccaccatga cggtggacag cctagtgaac aaggagtgct gcccacgcct 10080
gggtgcagag tcggccaatg tctgtggctc tcagcaaggc cgggggcagt gcacagaggt 10140
gcgagccgac acaaggccct ggagtggtcc ctacatccta cgaaaccagg atgaccgtga 10200
gctgtggcca agaaaattct tccaccggac ctgcaagtgc acaggaaact ttgccggcta 10260
taattgtgga gactgcaagt ttggctggac cggtcccaac tgcgagcgga agaaaccacc 10320
agtgattcgg cagaacatcc attccttgag tcctcaggaa agagagcagt tcttgggcgc 10380
cttagatctc gcgaagaaga gagtacaccc cgactacgtg atcaccacac aacactggct 10440
gggcctgctt gggcccaatg gaacccagcc gcagtttgcc aactgcagtg tttatgattt 10500
ttttgtgtgg ctccattatt attctgttag agatacatta ttaggaccag gacgccccta 10560
cagggccata gatttctcac atcaaggacc tgcatttgtt acctggcacc ggtaccattt 10620
gttgtgtctg gaaagagatc tccagcgact cattggcaat gagtcttttg ctttgcccta 10680
ctggaacttt gccactggga ggaacgagtg tgatgtgtgt acagaccagc tgtttggggc 10740
agcgagacca gacgatccga ctctgattag tcggaactca agattctcca gctgggaaac 10800

```
tgtctgtgat agcttggatg actacaacca cctggtcacc ttgtgcaatg gaacctatga  10860
aggtttgctg agaagaaatc aaatgggaag aaacagcatg aaattgccaa ccttaaaaga  10920
catacgagat tgcctgtctc tccagaagtt tgacaatcct cccttcttcc agaactctac  10980
cttcagtttc aggaatgctt tggaagggtt tgataaagca gatgggactc tggattctca  11040
agtgatgagc cttcataatt tggttcattc cttcctgaac gggacaaacg ctttgccaca  11100
ttcagccgcc aatgatccca tttttgtggt tcttcattcc tttactgatg ccatctttga  11160
tgagtggatg aaaagattta atcctcctgc agatgcctgg cctcaggagc tggcccctat  11220
tggtcacaat cggatgtaca acatggttcc tttcttccct ccagtgacta atgaagaact  11280
ctttttaacc tcagaccaac ttggctacag ctatgccatc gatctgccag tttcagttga  11340
agaaactcca ggttggccca caactctctt agtagtcatg ggaacactgg tggctttggt  11400
tggtcttttt gtgctgttgg cttttcttca atatagaaga cttcgaaaag gatatacacc  11460
cctaatggag acacatttaa gcagcaagag atacacagaa gaagcctagt aggcgcgcgt  11520
tctagtgtga aatagacatc agaattaaga aaaacgtagg gtccaagtgg ttccccgtta  11580
tggactcgct atctgtcaac cagatcttat accctgaagt tcacctagat agcccgatag  11640
ttaccaataa gatagtagcc atcctggagt atgctcgagt ccctcacgct tacagcctgg  11700
aggaccctac actgtgtcag aacatcaagc accgcctaaa aaacggattt tccaaccaaa  11760
tgattataaa caatgtggaa gttgggaatg tcatcaagtc caagcttagg agttatccgg  11820
cccactctca tattccatat ccaaattgta atcaggattt atttaacata gaagacaaag  11880
agtcaacgag gaagatccgt gaactcctca aaaaggggaa ttcgctgtac tccaaagtca  11940
gtgataaggt tttccaatgc ttaagggaca ctaactcacg gcttggccta ggctccgaat  12000
tgagggagga catcaaggag aaagttatta acttgggagt ttacatgcac agctcccagt  12060
ggtttgagcc ctttctgttt tggtttacag tcaagactga gatgaggtca gtgattaaat  12120
cacaaaccca tacttgccat aggaggagac acacacctgt attcttcact ggtagttcag  12180
ttgagttgct aatctctcgt gaccttgttg ctataatcag taaagagtct caacatgtat  12240
attacctgac atttgaactg gttttgatgt attgtgatgt catagagggg aggttaatga  12300
cagagaccgc tatgactatt gatgctaggt atacagagct tctaggaaga gtcagataca  12360
tgtggaaact gatagatggt ttcttccctg cactcgggaa tccaacttat caaattgtag  12420
ccatgctgga gcctctttca cttgcttacc tgcagctgag ggatataaca gtagaactca  12480
gaggtgcttt ccttaaccac tgctttactg aaatacatga tgttcttgac caaaacgggt  12540
tttctgatga aggtacttat catgagttaa ctgaagctct agattacatt ttcataactg  12600
atgacataca tctgacaggg gagattttct catttttcag aagtttcggc caccccagac  12660
ttgaagcagt aacggctgct gaaaatgtta ggaaatacat gaatcagcct aaagtcattg  12720
tgtatgagac tctgatgaaa ggtcatgcca tattttgtgg aatcataatc aacggctatc  12780
gtgacaggca cggaggcagt tggccaccgc tgaccctccc cctgcatgct gcagacacaa  12840
tccggaatgc tcaagcttca ggtgaagggt taacacatga gcagtgcgtt gataactgga  12900
aatcttttgc tggagtgaaa tttggctgct ttatgcctct tagcctggat agtgatctga  12960
caatgtacct aaaggacaag gcacttgctg ctctccaaag ggaatgggat tcagtttacc  13020
cgaaagagtt cctgcgttac gaccctccca agggaaccgg gtcacggagg cttgtagatg  13080
ttttccttaa tgattcgagc tttgacccat atgatgtgat aatgtatgtt gtaagtggag  13140
```

cttacctcca tgaccctgag ttcaacctgt cttacagcct gaaagaaaag gagatcaagg 13200
aaacaggtag actttttgct aaaatgactt acaaaatgag ggcatgccaa gtgattgctg 13260
aaaatctaat ctcaaacggg attggcaaat attttaagga caatgggatg gccaaggatg 13320
agcacgattt gactaaggca ctccacactc tagctgtctc aggagtcccc aaagatctca 13380
aagaaagtca caggggggg ccagtcttaa aaacctactc ccgaagccca gtccacacaa 13440
gtaccaggaa cgtgagagca gcaaaagggt ttatagggtt ccctcaagta attcggcagg 13500
accaagacac tgatcatccg gagaatatgg aagcttacga gacagtcagt gcatttatca 13560
cgactgatct caagaagtac tgccttaatt ggagatatga gaccatcagc ttgtttgcac 13620
agaggctaaa tgagatttac ggattgccct catttttcca gtggctgcat aagaggcttg 13680
agacctctgt cctgtatgta agtgaccctc attgcccccc cgaccttgac gcccatatcc 13740
cgttatataa agtccccaat gatcaaatct tcattaagta ccctatggga ggtatagaag 13800
ggtattgtca gaagctgtgg accatcagca ccattcccta tctatacctg gctgcttatg 13860
agagcggagt aaggattgct tcgttagtgc aaggggacaa tcagaccata gccgtaacaa 13920
aaagggtacc cagcacatgg ccctacaacc ttaagaaacg ggaagctgct agagtaacta 13980
gagattactt tgtaattctt aggcaaaggc tacatgatat tggccatcac ctcaaggcaa 14040
atgagacaat tgtttcatca cattttttg tctattcaaa aggaatatat tatgatgggc 14100
tacttgtgtc ccaatcactc aagagcatcg caagatgtgt attctggtca gagactatag 14160
ttgatgaaac aagggcagca tgcagtaata ttgctacaac aatggctaaa agcatcgaga 14220
gaggttatga ccgttacctt gcatattccc tgaacgtcct aaaagtgata cagcaaattc 14280
tgatctctct tggcttcaca atcaattcaa ccatgacccg ggatgtagtc ataccctcc 14340
tcacaaacaa cgacctctta ataaggatgg cactgttgcc cgctcctatt gggggatga 14400
attatctgaa tatgagcagg ctgtttgtca gaaacatcgg tgatccagta acatcatcaa 14460
ttgctgatct caagagaatg attctcgcct cactaatgcc tgaagagacc ctccatcaag 14520
taatgacaca acaaccgggg gactcttcat tcctagactg ggctagcgac ccttactcag 14580
caaatcttgt atgtgtccag agcatcacta gactcctcaa gaacataact gcaaggtttg 14640
tcctgatcca tagtccaaac ccaatgttaa aaggattatt ccatgatgac agtaaagaag 14700
aggacgaggg actggcggca ttcctcatgg acaggcatat tatagtacct agggcagctc 14760
atgaaatcct ggatcatagt gtcacagggg caagagagtc tattgcaggc atgctggata 14820
ccacaaaagg cttgattcga gccagcatga ggaagggggg gttaacctct cgagtgataa 14880
ccagattgtc caattatgac tatgaacaat tcagagcagg gatggtgcta ttgacaggaa 14940
gaaagagaaa tgtcctcatt gacaaagagt catgttcagt gcagctggcg agagctctaa 15000
gaagccatat gtgggcgagg ctagctcgag gacggcctat ttacggcctt gaggtccctg 15060
atgtactaga atctatgcga ggccacctta ttcggcgtca tgagacatgt gtcatctgcg 15120
agtgtggatc agtcaactac ggatggtttt ttgtcccctc gggttgccaa ctggatgata 15180
ttgacaagga aacatcatcc ttgagagtcc catatattgg ttctaccact gatgagagaa 15240
cagacatgaa gcttgccttc gtaagagccc caagtcgatc cttgcgatct gctgttagaa 15300
tagcaacagt gtactcatgg gcttacggtg atgatgatag ctcttggaac gaagcctggt 15360
tgttggctag gcaaagggcc aatgtgagcc tggaggagct aagggtgatc actcccatct 15420
caacttcgac taatttagcg cataggttga gggatcgtag cactcaagtg aaatactcag 15480
gtacatccct tgtccgagtg gcgaggtata ccacaatctc caacgacaat ctctcatttg 15540

```
tcatatcaga taagaaggtt gatactaact ttatatacca acaaggaatg cttctagggt  15600
tgggtgtttt agaaacattg tttcgactcg agaaagatac cggatcatct aacacggtat  15660
tacatcttca cgtcgaaaca gattgttgcg tgatcccgat gatagatcat cccaggatac  15720
ccagctcccg caagctagag ctgagggcag agctatgtac caacccattg atatatgata  15780
atgcaccttt aattgacaga gatgcaacaa ggctatacac ccagagccat aggaggcacc  15840
ttgtggaatt tgttacatgg tccacacccc aactatatca cattttagct aagtccacag  15900
cactatctat gattgacctg gtaacaaaat ttgagaagga ccatatgaat gaaatttcag  15960
ctctcatagg ggatgacgat atcaatagtt tcataactga gtttctgctc atagagccaa  16020
gattattcac tatctacttg ggccagtgtg cggccatcaa ttgggcattt gatgtacatt  16080
atcatagacc atcagggaaa tatcagatgg gtgagctgtt gtcatcgttc ctttctagaa  16140
tgagcaaagg agtgtttaag gtgcttgtca atgctctaag ccacccaaag atctacaaga  16200
aattctggca ttgtggtatt atagagccta tccatggtcc ttcacttgat gctcaaaact  16260
tgcacacaac tgtgtgcaac atggtttaca catgctatat gacctacctc gacctgttgt  16320
tgaatgaaga gttagaagag ttcacatttc tcttgtgtga aagcgacgag gatgtagtac  16380
cggacagatt cgacaacatc caggcaaaac acttatgtgt tctggcagat ttgtactgtc  16440
aaccagggac ctgcccacca attcgaggtc taagaccggt agagaaatgt gcagttctaa  16500
ccgaccatat caaggcagag gctatgttat ctccagcagg atcttcgtgg aacataaatc  16560
caattattgt agaccattac tcatgctctc tgacttatct ccggcgagga tcgatcaaac  16620
agataagatt gagagttgat ccaggattca ttttcgacgc cctcgctgag gtaaatgtca  16680
gtcagccaaa gatcggcagc aacaacatct caaatatgag catcaaggct ttcagacccc  16740
cacacgatga tgttgcaaaa ttgctcaaag atatcaacac aagcaagcac aatcttccca  16800
tttcaggggg caatctcgcc aattatgaaa tccatgcttt ccgcagaatc gggttgaact  16860
catctgcttg ctacaaagct gttgagatat caacattaat taggagatgc cttgagccag  16920
gggaggacgg cttgttcttg ggtgagggat cgggttctat gttgatcact tataaagaga  16980
tacttaaact aaacaagtgc ttctataata gtggggtttc cgccaattct agatctggtc  17040
aaagggaatt agcaccctat ccctccgaag ttggccttgt cgaacacaga atgggagtag  17100
gtaatattgt caaagtgctc tttaacggga ggcccgaagt cacgtgggta ggcagtgtag  17160
attgcttcaa tttcatagtt agtaatatcc ctacctctag tgtggggttt atccattcag  17220
atatagagac cttgcctgac aaagatacta tagagaagct agaggaattg gcagccatct  17280
tatcgatggc tctgctcctg ggcaaaatag gatcaatact ggtgattaag cttatgcctt  17340
tcagcgggga ttttgttcag ggatttataa gttatgtagg gtctcattat agagaagtga  17400
accttgtata ccctagatac agcaacttca tctctactga atcttatttg gttatgacag  17460
atctcaaggc taaccggcta atgaatcctg aaaagattaa gcagcagata attgaatcat  17520
ctgtgaggac ttcacctgga cttataggtc acatcctatc cattaagcaa ctaagctgca  17580
tacaagcaat tgtgggagac gcagttagta gaggtgatat caatcctact ctgaaaaaac  17640
ttacacctat agagcaggtg ctgatcaatt gcgggttggc aattaacgga cctaagctgt  17700
gcaaagaatt gatccaccat gatgttgcct cagggcaaga tggattgctt aattctatac  17760
tcatcctcta cagggagttg gcaagattca aagacaacca aagaagtcaa caagggatgt  17820
tccacgctta ccccgtattg gtaagtagca ggcaacgaga acttatatct aggatcaccc  17880
```

-continued

```
gcaaattctg ggggcacatt cttctttact ccgggaacaa aaagttgata aataagttta  17940

tccagaatct caagtccggc tatctgatac tagacttaca ccagaatatc ttcgttaaga  18000

atctatccaa gtcagagaaa cagattatta tgacgggggg tttgaaacgt gagtgggttt  18060

ttaaggtaac agtcaaggag accaaagaat ggtataagtt agtcggatac agtgccctga  18120

ttaaggacta attggttgaa ctccggaacc ctaatcctgc cctaggtggt taggcattat  18180

ttgcaatata ttaaagaaaa ctttgaaaat acgaagtttc tattcccagc tttgtctggt  18240
```

MEASLES VIRUS ENCODING A TUMOR ANTIGEN

The present invention relates to a recombinant virus of the family Paramyxoviridae comprising an expressible polynucleotide encoding at least one of (i) a tumor antigen, (ii) a fragment of a tumor antigen, and (iii) a variant of (i) or (ii). The present invention further relates to a polynucleotide encoding said recombinant virus of the family Paramyxoviridae and to a host cell comprising said recombinant virus of the family Paramyxoviridae and/or said polynucleotide encoding said recombinant virus of the family Paramyxoviridae. Moreover, the present invention relates to a method for activating immune cells with antitumor activity in a sample comprising cancer cells and to further means, methods, and uses related to the present invention.

Oncolytic viruses (OV) which replicate selectively in tumor cells are an emerging modality of cancer treatment. Aside from direct cytopathic effects and lysis of tumor cells, interactions of OV with the immune system can trigger systemic anti-tumor immunity. OV have been modified to express immunomodulatory transgenes to further enhance these effects (Melcher et al., Mol Ther. 2011, 19: 1008-1016). The vaccinia virus JX-594 and herpesvirus talimogene laherpavec (TVEC), both harboring GM-CSF, have shown promising results in clinical phase II and III trials (Heo et al., Nat Med. 2013, 19: 329-336 and Andtbacka et al. J Clin Oncol. 2013, 31, suppl; abstr LBA9008).

RNA viruses, in particular members of the family Paramyxoviridae like, e.g. measles virus, have also shown potential use in oncolysis. Viruses of the family Paramyxoviridae are negative-sense single-stranded RNA viruses and include human pathogens like, e.g. human parainfluenza viruses, mumps virus, human respiratory syncytial virus, and measles virus. From wild type measles virus, several non-pathogenic strains, including a vaccine strain, have been derived, which have been shown to remain oncolytic. The measles virus vaccine strain has been developed as a vector platform to target multiple tumor entities and several clinical trials are ongoing (Russell et al., Nat Biotechnol. 2012, 30: 658-670). Recently, the capacity of oncolytic MV encoding GM-CSF to support the induction of a specific anti-tumor immune response in terms of a tumor vaccination effect was demonstrated (Grossardt et al. Hum Gene Ther. 2013, 24: 644-654).

Tumor antigens, i.e. antigenic compounds associated with cancer cells, have been identified early in tumor research. Initially, the term "tumor antigen" was used to relate to antigens expressed by tumor cells relatively specifically, while the term "tumor specific antigen" was used to relate to structures exclusively found on tumors. However, this distinction was later given up in view of the vast diversity of expression profiles in tumors. Tumor antigens have been known as tumor markers, but also as targets useful for targeting cancer cells with high specificity. MV oncolytic specificity can be achieved by entry-targeting based on single-chain antibodies displayed on the viral attachment protein H blinded for its natural receptors CD46 and SLAM (Vongpunsawad et al. (2004), J Virol 78: 302; Nakamura et al. (2004), Nat Biotechnol 22: 331). To date, a wide variety of tumor antigen-specific MV have been generated including vectors with specificity for CD20, CD38, CEA, PSCA, PSMA, EGFR, EGFRvIII, Her2neu, HMWAA (cf. Hammond et al. (2001), J Virol 75(5): 2087. (PMID: 11160713); Peng et al. (2003), Blood 101(7): 2557 (PMID: 12433686); Allen et al. (2006), Cancer Res 66(24): 11840 (PMID: 17178881); Hasegawa et al. (2007), J Virol. 81(23): 13149

(PMID: 17804513); Ungerechts (2007), Cancer Res. 67(22): 10939 (PMID: 18006839); Liu et al. (2009), Prostate 69(10): 1128 (PMID: 19367568); Bossow et al. (2011), Cancer Gene Ther. 18(8): 598 (PMID: 21701532); Zaoui et al. (2012), Cancer Gene Ther. 19(3): 181-91 (PMID: 22076043); Kaufmann et al. (2013), J Invest Dermatol. 133(4): 1034 (PMID: 23223133)).

There is, however, still a need in the art for improved cancer therapies, in particular for improved oncolytic viruses.

Accordingly, the present invention relates to a recombinant virus of the family Paramyxoviridae comprising an expressible polynucleotide encoding at least one of (i) a tumor antigen, (ii) a fragment of a tumor antigen, and (iii) a variant of (i) or (ii).

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value±20%, more preferably ±10%, most preferably ±5%.

The term "recombinant virus", as used herein, relates to a virus comprising a genome modified by biotechnological means as compared to known, naturally occurring, virus genomes. Preferably, the recombinant virus is a virus comprising a genome modified as compared to naturally occurring virus genomes. Preferred biotechnological means for modifying a viral genome are known to the skilled person and include any of the methods of molecular cloning, in particular recombinant DNA techniques including, without limitation, cleavage of DNA by restriction enzymes, ligation of DNA, polymerase chain reaction (PCR), cloning of viral genomes, and the like. It is understood by the skilled person that viruses of the family Paramyxoviridae have a single-stranded (−)-RNA as a genome. Accordingly, the genome of the recombinant virus of the present invention, preferably, is obtained by cloning an expression vector as described herein below comprising an expressible nucleotide sequence encoding said recombinant virus genome, followed by expressing said expressible nucleotide sequence encoding said recombinant virus in a permissive host cell. Alternatively, the recombinant virus genome may also be expressed in non-permissive host cells, e.g., preferably, from rodents or other higher eukaryotes. Preferably, the recombinant virus of the present invention is a recombinant virus of the family Paramyxoviridae, more preferably a recombinant Morbillivirus, most preferably, a recombinant measles virus (MV). As will be understood by the skilled person, the recombinant virus of the present invention may comprise further modifications as compared to a naturally occurring virus. Preferably, the recombinant virus comprises a polypeptide mediating a modified tropism and/or a polynucleotide encoding the same. More preferably, said polypeptide mediating a modified tropism is a fusion polypeptide of a viral membrane integral polypeptide or of a viral membrane associated polypeptide with a polypeptide mediating binding to a target, e.g. a cell, preferably a specific kind of cell, more preferably a cancer cell. Preferably, said fusion polypeptide comprises a viral hemagglutinin or a fragment thereof, preferably a membrane integral fragment thereof. Preferably, said fusion polypeptide comprises a single-chain antibody specifically binding to a target molecule, e.g. to Carcinoembryonic antigen (CEA) or CD20. Most preferably, said fusion polypeptide is a fusion polypeptide of a truncated viral hemagglutinin with an anti-CD20 single-chain antibody or with an anti-CEA single-chain antibody. Preferably, the recombinant virus comprises a polynucleotide comprising the nucleic acid sequence of any one of SEQ ID NOs: 3 to 5.

As used herein, the term "activator of the immune response" relates to a compound which, when contacted with a mixture of immune cells and immune-response inducing cells, e.g. cancer cells, causes at least one type of immune cell to be more active as compared to an immune cell of the same type comprised in the same mixture but lacking said compound. Preferably, the immune cell activated is a cell mediating a response increasing a subject's resistance to an antigen, i.e. preferably, said immune cell is not a tolerance-mediating immune cell. Preferably, the immune cell activated by the activator of the immune response is a T-cell, more preferably a helper T-cell or a cytotoxic T-cell. Most preferably, the immune cell activated by the activator of the immune response is a cytotoxic T-cell expressing PD-1. Measures of immune cell activity are known to the skilled person and include, preferably, expression of activation markers, production of antibodies, excretion of cytokines, and release of cytotoxins, e.g. perforin, granzymes, and/or granolysin. As used herein, a tumor antigen does not have the activity of being an activator of the immune response; thus, preferably, a tumor antigen is not an activator of the immune response.

Preferably, the activator of the immune response is an activatory chemokine, preferably an activatory interleukin, more preferably IL-12. Also preferably, the activator of the immune response is an antagonist of a signaling pathway causing at least one type of immune cell to become inhibited. Accordingly, preferably, the activator of the immune response is a ligand for an immune checkpoint blockade protein. More preferably, the activator of the immune response is a ligand for an immune checkpoint blockade protein. Still more preferably, the activator of the immune response is an inhibitor of PD-1 receptor signaling. It is understood by the skilled person that signaling through a receptor signaling pathway can be inhibited by either preventing the receptor from being activated, or by preventing the signal generated by the activated receptor from being further transmitted. Accordingly, preferably, the activator of the immune response is a PD-L1 antagonist, the term "antagonist" relating to a compound binding to the molecule the effect of which is antagonized and through said binding preventing said molecule from interacting with its native binding partner in a productive, i.e. signaling-inducing, way. Preferred assays for said activity are described e.g. in WO 2015/128313 A1.

The term "immune response", as used herein, relates to any protective response of the body of a subject to an antigen involving activity of at least one type of leukocyte, preferably lymphocyte, and/or of at least one antigen-recognizing macromolecule. Preferably, the immune response comprises inactivation of said antigen by production of antigen-specific antibodies (humoral immune response). More preferably, the immune response comprises lysis of foreign cells or of body cells, preferably of cancer cells, presenting said antigen (cell-mediated immune response).

The term "modulating the immune response", as used herein, relates to inducing a change in, preferably an activation of, the response of a subject's adaptive immune system. Accordingly, the term "modulating the immune response", preferably, relates to (i) newly inducing an immune response of a subject to an antigen, (ii) to inducing an increase in the quality or intensity of the immune response of a subject to an antigen, and/or to (iii) redirecting an existing immune response to a target cell of interest, preferably a cancer cell, more preferably a cancer cell comprising a tumor antigen. Preferably, modulating an immune response includes or is presenting an antigen or epitope on a cell in the context of at least one of major histocompatibility complex (MHC) class I (MHC-I) and MHC class II (MHC-II) molecules. Preferably, the modulation is an activation, i.e. leads to an enhanced response to the antigen. Also preferably, modulating an immune response includes or is increasing the frequency of antigen-specific T-cells in the blood of a subject. More preferably, modulating an immune response is increasing the frequency of antigen-specific CD-4+ and/or CD-8+ T-cells in the blood of said subject. Most preferably, modulating an immune response is increasing the frequency of activated antigen-specific CD-4+ and/or CD-8+ T-cells in the blood of said subject. Preferably, said modulating an immune response against an antigen induces killing of cells expressing said antigen by the immune system of the subject. More preferably, the term relates to inducing regression of at least one cancer comprising cells expressing said antigen. It is to be understood that inducing an immune response may not be effective in all subjects; e.g. in case a single specific epitope of a polypeptide is used as an antigen, a subject may lack MHC molecules suitable for effectively displaying said epitope. The skilled person knows how to improve immune reaction in such case, e.g. by including further epitopes into the recombinant virus of the family Paramyxoviridae.

The term "antigen" is known to the skilled person and relates to a chemical compound modulating an immune response in a host organism, wherein said host organism, preferably, is a vertebrate organism, preferably is a mammal, more preferably a human or an experimental animal, in particular a rat, a mouse, a rabbit, a guinea pig, a hamster, a sheep, a goat, a horse, a cow, a donkey, most preferably is a human.

Preferably, the antigen is an antigenic polypeptide. The term "antigenic polypeptide", as used herein, relates to a polypeptide comprising at least one antigenic epitope. Preferably, said antigenic epitope is a glycan portion of a polypeptide. More preferably, said antigenic epitope is a peptide and comprises a sequence of at least four, preferably at least five, more preferably at least six, most preferably at least seven amino acids. Also preferably, said antigenic epitope is a peptide and comprises a sequence of from four to 15, preferably of from five to twelve, more preferably of from six to ten, most preferably of from seven to nine amino acids. Preferably, the antigenic epitope is a T-cell epitope. A T-cell epitope, as is known to the one skilled in the art, is a contiguous sequence of amino acids comprised in a peptide, which can be bound to a MHC class I or class II molecule to be presented on the surface of a cell (MHC-I) or of a professional antigen presenting cell (MHC-II). The skilled artisan knows how to predict immunogenic peptides presented on MHC-I or MHC-II (Nielsen et al., (2004), Bioinformatics, 20 (9), 1388-1397), Bordner (2010), PLoS ONE 5(12): e14383) and how to evaluate binding of specific peptides (e.g. Bernardeau et al., (2011), J Immunol Methods, 371(1-2): 97-105). Preferably, the antigenic epitope is an MHC-II epitope.

The term "cancer", as used herein, relates to a disease of an animal, including man, characterized by uncontrolled growth by a group of body cells ("cancer cells"). This uncontrolled growth may be accompanied by intrusion into and destruction of surrounding tissue and possibly spread of cancer cells to other locations in the body. Preferably, also included by the term cancer is a relapse. Thus, preferably, the cancer is a solid cancer, a metastasis, or a relapse thereof.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, fibrosarcoma, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor. More preferably, the cancer is a solid cancer, a metastasis, or a relapse thereof. Most preferably, the cancer is a tumor derived from malignant melanoma, head and neck cancer, hepatocellular carcinoma, pancreatic carcinoma, prostate cancer, renal cell carcinoma, gastric carcinoma, colorectal carcinoma, a lymphoma or a leukemia.

The term "tumor antigen", as used herein, relates to any antigen comprised by a cancer cell. Thus, the term tumor antigen includes antigens comprised by cancer cells and by one or more non-cancer cell types, e.g. CD19, CD20, CD22, CD30, and CD33. Preferably, the tumor antigen is a tumor-associated antigen, i.e. an antigen expressed by cancer cells, but not by normal cells of the same type as the cancer cells in said subject. Also preferably, the tumor antigen is a tumor-specific antigen, i.e. an antigen expressed by cancer cells, but not by normal, i.e. non-cancer, cells of said subject at the given development stage. Also preferably, the tumor antigen is a neoantigen, i.e. an antigen not encoded in the germ line of said subject; preferably, said neoantigen is an antigen encoded by the tumor genome or an infectious agent, in particular a virus, preferably a tumorigenic virus, more preferably a papillomavirus, an Epstein-Barr virus, Hepatitis B virus, or Hepatitis C virus; or said neoantigen is a mutein comprised by a cancer cell, i.e. a polypeptide variant produced after a mutation of the encoding gene in the genome of said subject has occurred. As specified herein above, an antigen, and also a tumor antigen, has the biological activity of modulating an immune response in a host organism. Preferably, the tumor antigen has the biological activity of modulating an immune response in a human. Also preferably, the tumor antigen has the biological activity of modulating an immune response in the subject from which the cells comprising said tumor antigen are derived from. Preferably, the tumor antigen is a biological macromolecule, more preferably a polypeptide. Preferably, the tumor antigen is a human tumor antigen.

Preferably, the tumor antigen is selected from the group consisting of L-dopachrome-tautomerase (TRP2), melanocyte protein PMEL (gp100), HPV E6/7, MAGE 1, MAGE 3, NY-ESO, androgen receptor (AR), BCL-1, calprotectin, carcinoembryonic antigen (CEA), EGFRs, epithelial cell adhesion molecule (Ep-CAM), epithelial sialomucin, membrane estrogen receptors (mER), FAP HER2/neu, human high molecular weight melanoma-associated antigen (HMW-MAA), IL-6, MOC-1, MOC-21, MOC-52, melan-A/MART-1, melanoma-associated antigen, mucin, OKT9, progesterone receptor (PGR), prostate specific antigen (PSA), prostate stem cell antigen (PSCA), prostate-specific membrane antigen (PSMA), symaptophysin, VEGFRs, CD19, CD20, CD22, CD30 and CD33. More preferably, the tumor antigen is HPV E6/7, MAGE 1, MAGE 3, NY-ESO, TRP2 or gp100, more preferably is TRP2. The open reading frame encoding human TRP2 is disclosed herein as SEQ ID NO: 1, the amino acid sequence of human TRP2 is disclosed as SEQ ID NO:2.

Preferably, the recombinant virus of the family Paramyxoviridae comprises an expressible polynucleotide encoding a fragment of a tumor antigen. As used herein, the term "fragment of a tumor antigen" relates to a substructure of a tumor antigen having the biological activity of modulating an immune response as specified herein above. Thus, the fragment of a tumor antigen, preferably, is an antigenic polypeptide as specified herein, comprising at least a subsequence of said tumor antigen polypeptide; preferably, the fragment of a tumor antigen comprises at least one antigenic epitope in such case, more preferably at least one epitope which is antigenic in the subject the cells comprising the tumor antigen are derived from. Preferably, a fragment of a tumor antigen is or is derived from, e.g., a degradation product or a splice variant of the tumor antigen. Preferably, the fragment of a tumor antigen comprises, preferably consists of: (i) a fragment of a human papillomavirus (HPV) E6 polypeptide, preferably of an E6 polypeptide of a high-risk HPV, e.g. of a HPV16 E6 (Genbank Acc No: NP_041325.1 GI: 9627104), (ii) a fragment of a HPV E7 polypeptide, preferably of an E7 polypeptide of a high-risk HPV, e.g. of a HPV16 E7 (Genbank Acc No: NP_041326.1 GI: 9627105); (iii) TRP2, preferably human TRP2 (preferably. encoded by Genbank Acc No: NM_001922.4 GI: 1015809739), (iv) cancer/testis antigen 1B (CTAG1B, also referred to as NY-ESO, preferably encoded by Genbank Acc No: NM_001327.2 GI: 215272337, or (v) an arbitrary combination of any of (i) to (iv).

Preferably, the recombinant virus of the family Paramyxoviridae comprises an expressible polynucleotide encoding a variant of a tumor antigen and/or of a fragment of a tumor antigen. As used herein, the term "variant" of a tumor antigen relates to an antigen being non-identical to said tumor antigen having the activity of modulating the immune response. Thus, as used herein, the term polypeptide "variant" relates to any chemical molecule comprising at least one polypeptide or fusion polypeptide as specified elsewhere herein, having the indicated activity, but differing in primary structure from said polypeptide or fusion polypeptide. Thus, the polypeptide variant, preferably, is a mutein having the indicated activity. Preferably, the polypeptide variant comprises a peptide having an amino acid sequence corresponding to an amino acid sequence of 5 to 200, more preferably 6 to 100, even more preferably 7 to 50, or, most preferably, 8 to 30 consecutive amino acids comprised in a polypeptide as specified above. Moreover, also encompassed are further polypeptide variants of the aforementioned polypeptides. Such polypeptide variants have at least essentially the same biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the whole length of the polypeptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to herein may be allelic variants or any other species specific homologs, paralogs, or orthologs; moreover, the polypeptide variants referred to herein include fragments of the specific polypeptides or the aforementioned types of polypeptide variants as long as these fragments and/or variants have the biological activity as referred to above. Further included are variants which differ due to posttranslational modifications such as phosphorylation, glycosylation, ubiquitinylation, sumoylation, or myristylation, by including non-natural amino acids, and/or by being peptidomimetics. Preferably, the variant of the tumor antigen or fragment of a tumor antigen comprises, preferably consists of, at least one of a variant of (i) a HPV E6 polypeptide, preferably of an E6 polypeptide of a high-risk HPV, e.g. of a HPV16 E6 (Genbank Acc No: NP_041325.1 GI: 9627104), (ii) a HPV E7 polypeptide, preferably of an E7 polypeptide of a high-risk HPV, e.g. of a HPV16 E7 (Genbank Acc No: NP_041326.1 GI: 9627105); (iii) TRP2, preferably human TRP2 (preferably. encoded by Genbank Acc No: NM_001922.4 GI: 1015809739), (iv) cancer/testis antigen 1B (CTAG1B, also referred to as NY-ESO, preferably encoded by Genbank Acc No: NM_001327.2 GI: 215272337), or (v) an arbitrary combination of any of (i) to (iv).

Preferably, the tumor antigen, fragment of a tumor antigen, or variant of tumor antigen is a fusion polypeptide comprising further amino acids or polypeptides. More preferably, the fusion polypeptide further comprises a detectable tag. The term "detectable tag" refers to a stretch of amino acids which are added to or introduced into the fusion polypeptide. Preferably, the tag is added C- or N-terminally to the fusion polypeptide. The said stretch of amino acids shall allow for detection of the fusion polypeptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art. In a further preferred embodiment, said fusion protein comprises a peptide or polypeptide comprising the amino acid sequence of a further tumor antigen or of an activator of the immune response.

The term "expressible polynucleotide", as used herein, relates to a polynucleotide operatively linked to at least one expression control sequence causing transcription of the nucleic acid sequence comprised in said polynucleotide to occur, preferably in eukaryotic cells or isolated fractions thereof, preferably into a translatable mRNA or into a viral genome. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Preferably, the aforesaid at least one expression control sequence is an expression control sequence of a (−)strand RNA virus, more preferably of a Paramyxovirus as described herein above, most preferably of an MV. Thus, preferably, at least one expression control sequence comprises a (−)strand RNA viral regulatory sequence ensuring initiation of transcription (consensus "gene start signal", preferably consensus MV "gene start signal") and termination signals (consensus "gene stop signal", preferably, consensus MV "gene stop signal") ensuring termination of transcription and stabilization of the transcript. It is known in the art that production of viral particles in permissive host cells can be initiated by transfecting into said permissive host cells one or more expressible DNA constructs encoding (i) a recombinant viral anti-genome, (ii) the viral L gene, (iii) the viral P gene, and (iv) the viral N gene. It is also understood by the skilled person that, once a viral genome and the aforesaid viral genes were expressed in said host cell, replication and assembly of viral particles occurs in the cytoplasm of the host cell and is, therefore, solely dependent on viral regulatory signals. Preferably, production of viral particles in permissive host cells may also be initiated by transfecting into said permissive host cells one or more expressible DNA (i) a construct encoding a recombinant viral anti-genome and introducing into said permissive host cells the polypeptide products of (ii) the viral L gene, (iii) the viral P gene, and (iv) the viral N gene. The term polynucleotide, as used herein, preferably encompasses polynucleotide variants as specified elsewhere herein. Preferably, the expressible polynucleotide encoding the polynucleotides of the invention, preferably (i) a tumor antigen, (ii) a fragment of a tumor antigen, or (iii) a variant of (i) or (ii), is comprised in the genome of the recombinant virus of the family Paramyxoviridae in a region corresponding to the region intervening the H and the L gene of measles virus. Preferably, the expressible polynucleotide comprises further coding sequences. More preferably, the expressible polynucleotide encodes an activator of the immune response. In an embodiment, the expressible polynucleotide encodes at least one further of (i) a tumor antigen, (ii) a fragment of a tumor antigen, and (iii) a variant of (i) or (ii). As will be understood, the further polypeptides encoded may be encoded as separate polypeptides or as fusion polypeptides comprising at least one, preferably at least two, more preferably at least three of (i) a tumor antigen, (ii) a fragment of a tumor antigen, and (iii) a variant of (i) or (ii). Thus, preferably, the expressible polynucleotide may encode a multitude of antigenic epitopes of tumor antigens as one or more fusion polypeptide(s). In a further embodiment, said activator of the immune response comprises, preferably is, a secreted soluble activator of the immune response, preferably an immunoglobulin or fragment thereof, more preferably a secreted immunoglobulin or fragment thereof.

As used herein, the term "immunoglobulin" relates to a polypeptide being a soluble immunoglobulin, preferably an antibody from any of the classes IgA, IgD, IgE, IgG, or IgM, preferably having the activity of binding, more preferably specifically binding, a molecule of interest. Immunoglobulins against antigens of interest can be prepared by well-known methods using, e.g., a purified molecule of interest or a suitable fragment derived therefrom as an antigen. A fragment which is suitable as an antigen may be identified by antigenicity determining algorithms well known in the art. Such fragments may be obtained either from one of the molecules of interest by proteolytic digestion, may be a synthetic peptide, or may be obtained by recombinant expression. Preferably, a peptide of a molecule of interest used as an antigen is located at the exterior of a cell expressing the molecule of interest; i.e. preferably, the epitope the binding domain interacts with, preferably, is an extracellular domain. Preferably, the immunoglobulin of the present invention is a monoclonal antibody, a human or humanized antibody or primatized, chimerized antibody or a fragment thereof, so long as they exhibit the desired binding activity as specified elsewhere herein. Also comprised as antibodies of the present invention are a bispecific antibody, a synthetic antibody, or a chemically modified derivative of any of these. Preferably, the antibody of the present invention shall specifically bind (i.e. does only to a negligible extent or, preferably, not cross react with other polypeptides or peptides) to a molecule of interest as specified above. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Kohler and Milstein, Nature. 1975. 256: 495; and Galfré, Meth. Enzymol. 1981, 73: 3, which comprise the fusion of mouse myeloma cells to spleen cells derived from immunized mammals. As will be understood by the skilled person, a molecule of interest, bound by an immunoglobulin of the present invention, may also be an Fc receptor or a complement protein binding an Fc part of an antibody; accordingly, the immunoglobulin preferably is an Fc domain of an antibody, more preferably a soluble Fc domain of an antibody, most preferably a secreted soluble Fc domain of an antibody. Preferably, said antibody the Fc domain is derived from is an IgG, more preferably an IgG1, most preferably a human IgG1.

"Immunoglobulin fragments" comprise a portion of an intact immunoglobulin, preferably of an antibody, in an embodiment, comprise the antigen-binding region thereof. Examples of antibody fragments and fusion proteins of variable regions include Fab, Fab', F(ab')2, and Fv fragments; diabodies; linear antibodies; single-chain antibody molecules; single-domain-antibodies (VHH), also known as nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. Preferably, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs, also referred to as complementarity determining regions (CDRs)) of each variable domain interact to define an antigen-binding site. Collectively, the six HVRs of one scFv confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "secreted", as used herein, relates to a compound being transferred from the interior of a host cell to the exterior of said host cell by a mechanism intrinsic to said host cell. Preferably, secretion of a polypeptide or fusion polypeptide is mediated by a, preferably eukaryotic, signal peptide mediating import of said peptide or polypeptide into the lumen of the endoplasmic reticulum and, more preferably, by the absence of retention signals. Signal peptides causing secretion of peptides or polypeptides are known in the art. Preferably, the signal peptide is an IL-12 signal peptide. Also preferably, the signal peptide is or comprises an Ig leader sequence. More preferably, the signal peptide is or comprises a human Ig leader sequence. Still more preferably, the signal peptide is or comprises a matching leader sequence, i.e. a leader sequence selected from the same Ig kappa subgroup as the variable light chain of the antibody, preferably, of the single-chain antibody.

Advantageously, it was found in the work underlying the present invention that recognition of tumor antigens not recognized by the immune system can be induced by presenting said tumor antigens in the context of a virus infection. Without wishing to be bound by theory, it is presumed that expression of tumor antigens in the context of a measles virus infection breaks tumor-induced tolerance and makes and immune response to the tumor antigen possible. Moreover, it was found that the expression of tumor antigens on tumor cells induced by measles virus infection increases infiltration and persistence of T-cells in tumors.

The definitions made above apply mutatis mutandis to the following. Additional definitions and explanations made further below also apply for all embodiments described in this specification mutatis mutandis.

The present invention further relates to polynucleotide encoding the recombinant virus of the family Paramyxoviridae according to the present invention The term "polynucleotide" is understood by the skilled person to relate to a polymer composed of a series of contiguous nucleotides; the term encompasses single as well as double stranded polynucleotides. Preferably, comprised are also chemically modified polynucleotides including naturally occurring modified polynucleotides such as glycosylated or methylated polynucleotides or artificial modified ones such as biotinylated polynucleotides and polynucleotides comprising modified nucleotides. Preferably, the nucleotides comprised in the polynucleotide are naturally occurring nucleotides. Preferably, the polynucleotide is RNA, including mRNA, or DNA, including cDNA. More preferably, the polynucleotide is DNA. Preferably, the nucleotides comprised in the polynucleotide comprise, preferably comprise exclusively, the bases adenine, guanine, cytosine, and thymine in case the polynucleotide is DNA; also preferably, the nucleotides comprised in the polynucleotide comprise, preferably comprise exclusively, the bases adenine, guanine, cytosine, and uracil in case the polynucleotide is RNA. The polynucleotides of the present invention either consist of, essentially consist of, or comprise the indicated nucleic acid sequences. Thus, they may contain further nucleic acid sequences as well. The polynucleotide of the present invention shall be provided, preferably, either as an isolated polynucleotide (i.e. isolated from its natural context) or in genetically modified form.

The term "polynucleotide encoding a recombinant virus", as used herein, relates to a polynucleotide comprising a nucleic acid sequence or nucleic acid sequences sufficient for generating a virus particle or a virus-like particle in a host cell. It is understood by the skilled person that a virus is constituted by a polynucleotide genome and at least one kind of capsid polypeptide. Accordingly, the polynucleotide encoding a recombinant virus of the present invention, preferably, comprises a recombinant virus genome. As will be understood by the skilled person, in case the polynucleotide encoding a recombinant virus is comprised in a virus according to the present invention, i.e. a virus of the family Paramyxoviridae, the polynucleotide is (−)strand RNA. It is also understood by the skilled person that in case the polynucleotide is DNA comprised in a host cell, at least an RNA-dependent RNA polymerase activity will additionally be required to produce viral particles from said DNA polynucleotide. Preferably, the polynucleotide encoding a recombinant virus comprises or consists of the nucleic acid sequence as specified elsewhere herein. As annotated herein, the sequence of the DNA copy of negative-strand (−)RNA viruses is annotated in the usual 5'→3'-orientation; this corresponds to the viral sequence in antigenomic (+)RNA orientation with respect to the natural 3'→5'-orientation of negative-strand (−)RNA viruses. Preferably, the polynucleotide encoding a recombinant virus is based on Measles virus strain Edmonston (Moraten vaccine), Genbank Acc No: AF266287.1 GI: 9181873. More preferably, the polynucleotide encoding a recombinant virus comprises, preferably consists of, the nucleic acid sequence of any one of SEQ ID NOs: 3 to 5.

The term polynucleotide, preferably, includes polynucleotide variants. The term "polynucleotide variant", as used herein, relates to a variant of a polynucleotide related to herein comprising a nucleic acid sequence characterized in that the sequence can be derived from the aforementioned specific nucleic acid sequence by at least one nucleotide substitution, addition and/or deletion, wherein the polynucleotide variant shall have the activity as specified for the specific polynucleotide. Preferably, said polynucleotide variant is an ortholog, a paralog or another homolog of the specific polynucleotide. Also preferably, said polynucleotide variant is a naturally occurring allele of the specific polynucleotide. Polynucleotide variants also encompass polynucleotides comprising a nucleic acid sequence which is capable of hybridizing to the aforementioned specific polynucleotides, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, or plants preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still encode a polypeptide or fusion polypeptide which still has the activity as specified. Accordingly, the polypeptide encoded may comprise or consist of the domains of the polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences.

The present invention further relates to a host cell comprising the recombinant virus of the family Paramyxoviridae according to the present invention and/or the polynucleotide encoding the recombinant virus of the family Paramyxoviridae according to the present invention.

As used herein, the term "host cell" relates to a vertebrate cell. Preferably, the cell is a vertebrate cell, preferably is a mammalian cell, more preferably a human cell or a cell of an experimental animal, in particular a rat, a mouse, a rabbit, a guinea pig, a hamster, a sheep, a goat, a horse, a cow, a donkey cell, most preferably is a human cell. Preferably, the host cell is a cancer cell, more preferably a tumor cell.

Further, the present invention relates to a medicament comprising (a) (i) a recombinant virus of the family Paramyxoviridae according to the present invention, (ii) a polynucleotide encoding the recombinant virus of the family Paramyxoviridae according to (i), preferably a polynucleotide according to an embodiment as specified herein below;

(iii) a host cell comprising the recombinant virus of the family Paramyxoviridae according to (i) and/or a polynucleotide encoding the recombinant virus of the family Paramyxoviridae according to (ii); preferably a host cell according to an embodiment as specified herein below; or (iv) any combination of (i) to (iii); and (b) at least one pharmacologically acceptable excipient.

The terms "medicament" and "pharmaceutical composition", as used herein, relate to the compounds of the present invention and optionally one or more pharmaceutically acceptable carrier, i.e. excipient. The compounds of the present invention can be formulated as pharmaceutically acceptable salts. Acceptable salts comprise acetate, methyl ester, HCl, sulfate, chloride and the like. The pharmaceutical compositions are, preferably, administered locally, topically or systemically. Suitable routes of administration conventionally used for drug administration are oral, intravenous, or parenteral administration as well as inhalation. A preferred route of administration is intra-tumoral administration. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The excipient(s) must be acceptable in the sense of being compatible with the other ingredients of the formulation and being not deleterious to the recipient thereof. The excipient employed may be, for example, a solid, a gel or a liquid carrier. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 μg for a polypeptide or polynucleotide, or 104-108 viral particles for a virus or a virus-like particle; however, doses below or above this exemplary range are envisioned, especially considering the aforementioned factors. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The present invention further relates to a method for activating immune cells with antitumor activity in a sample comprising cancer cells and immune cells, comprising a) contacting said sample comprising cancer cells and immune cells with
   (i) a recombinant virus of the family Paramyxoviridae according to the present invention,
   (ii) a polynucleotide encoding the recombinant virus of the family Paramyxoviridae according to (i), preferably a polynucleotide according to an embodiment as specified herein below;
   (iii) a host cell comprising the recombinant virus of the family Paramyxoviridae according to (i) and/or a polynucleotide encoding the recombinant virus of the family Paramyxoviridae according to (ii); preferably a host cell according to an embodiment as specified herein below; or
   (iv) any combination of (i) to (iii); and thereby,
b) activating immune cells with antitumor activity comprised in said sample.

The method for activating immune cells of the present invention, preferably, may comprise steps in addition to those explicitly mentioned above. For example, further steps may relate, e.g., to providing a sample for step a), or administration of additional compounds to the immune cells, e.g. immunostimulatory compounds before or during step b). Moreover, one or more of said steps may be performed by automated equipment. The method for activating immune cells of the present invention, preferably, is an in vitro method.

The term "contacting", as used in the context of the methods of the present invention, is understood by the skilled person. Preferably, the term relates to bringing a compound, e.g. a virus, a sample, or a subject of the present invention in physical contact with a further compound and thereby allowing the compound and the further compound to interact.

The term "immune cells", as used herein, relates cells mediating an immune response in a subject. Preferably, the immune cell is a leukocyte, preferably a lymphocyte. Preferably, the immune cell is a B-cell; more preferably, the immune cell is a T-cell, still more preferably a cytotoxic T cell or a T helper cell.

The present invention further relates to a method for treating cancer in a subject afflicted with cancer, comprising 1. a) contacting said subject with
2. (i) a recombinant virus of the family Paramyxoviridae according to the present invention,
3. (ii) a polynucleotide encoding the recombinant virus of the family Paramyxoviridae according to (i), preferably a polynucleotide according to an embodiment as specified herein;
4. (iii) a host cell comprising the recombinant virus of the family Paramyxoviridae according to (i) and/or a polynucleotide encoding the recombinant virus of the family Paramyxoviridae according to (ii); preferably a host cell according to an embodiment as specified herein; or
5. (iv) any combination of (i) to (iii); and, thereby, b) treating cancer in a subject afflicted with cancer.

The method of treatment of the present invention, preferably, may comprise steps in addition to those explicitly mentioned above. For example, further steps may relate, e.g., to localizing a tumor and/or diagnosing cancer for step a), or administration of additional medication for step b). More preferably, the method of treatment further comprises the steps of the method for activating immune cells as specified elsewhere herein, and the further step of administering said activated immune cells with antitumor activity to said subject. Moreover, one or more of said steps may be performed by automated equipment. The method of the present invention, preferably, is an in vivo method of treatment. Preferably, in the method of treatment, the cancer is a solid cancer, a metastasis, or a relapse thereof.

The term “treating” refers to ameliorating the diseases or disorders referred to herein or the symptoms accompanied therewith to a, preferably, significant extent. Said treating as used herein also includes an entire restoration of the health with respect to the diseases or disorders referred to herein. It is to be understood that treating as used in accordance with the present invention may not be effective in all subjects to be treated. However, the term shall, preferably, require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student’s t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating cancer is reducing tumor burden in a subject. As will be understood by the skilled person, effectiveness of treatment of e.g. cancer is dependent on a variety of factors including, e.g. cancer stage and cancer type. Preferably, treating cancer is reducing tumor burden.

Moreover, the present invention relates to a preparation of activated immune cells with antitumor activity obtained or obtainable by the method for activating immune cells of the present invention.

Furthermore, the present invention relates to the use of 1. (i) a recombinant virus of the family Paramyxoviridae according to the present invention,
2. (ii) a polynucleotide encoding the recombinant virus of the family Paramyxoviridae according to (i), preferably a polynucleotide according to an embodiment as specified herein below;
3. (iii) a host cell comprising the recombinant virus of the family Paramyxoviridae according to (i) and/or a polynucleotide encoding the recombinant virus of the family Paramyxoviridae according to (ii); preferably a host cell according to an embodiment as specified herein below; or
4. (iv) any combination of (i) to (iii);

for the manufacture of a medicament, preferably for the manufacture of a medicament for treating inappropriate cell proliferation.

Also, the present invention relates to a recombinant virus of the family Paramyxoviridae according to the present invention and/or a polynucleotide according to the present invention and/or a host cell according to the present invention for use in medical treatment. The present invention further relates to a recombinant virus of the family Paramyxoviridae according to the present invention and/or a polynucleotide according to the present invention and/or a host cell according to the present invention for use in treatment of inappropriate cell proliferation. Preferably, treatment of inappropriate cell proliferation is cancer treatment.

The present invention also relates to a kit comprising 1. (i) a recombinant virus of the family Paramyxoviridae according of any one of claims 1 to 20,
2. (ii) a polynucleotide encoding the recombinant virus of the family Paramyxoviridae according to (i), preferably a polynucleotide according to an embodiment as specified below;
3. (iii) a host cell comprising the recombinant virus of the family Paramyxoviridae according to (i) and/or a polynucleotide encoding the recombinant virus of the family Paramyxoviridae according to (ii); preferably a host cell according to an embodiment as specified below; or
4. (iv) any combination of (i) to (iii);

housed in a container.

The term “kit”, as used herein, refers to a collection of the aforementioned components. Preferably, said components are combined with additional components, preferably within an outer container. The outer container, also preferably, comprises instructions for carrying out a method of the present invention. Examples for components of the kit as well as methods for their use have been given in this specification. The kit, preferably, contains the aforementioned components in a ready-to-use formulation. Preferably, the kit may additionally comprise instructions, e.g., a user’s manual for applying the recombinant virus of the family Paramyxoviridae with respect to the applications provided by the methods of the present invention. Details are to be found elsewhere in this specification. Additionally, such user’s manual may provide instructions about correctly using the components of the kit. A user’s manual may be provided in paper or electronic form, e.g., stored on CD or CD ROM. The present invention also relates to the use of said kit in any of the methods according to the present invention.

Also, the present invention relates to a method for selecting (i) a recombinant virus of the family Paramyxoviridae comprising an expressible polynucleotide encoding a tumor antigen or a fragment or variant thereof, (ii) a polynucleotide encoding the recombinant virus of (i), and/or (iii) a host cell comprising the recombinant virus according to (i) and/or a polynucleotide according to (ii) for treating a subject suffering from cancer, said method comprising a) detecting at least one tumor antigen expressed by cancer cells in a cancer sample of said subject; and,
b) based on the determination of step a), selecting a recombinant virus, a polynucleotide and/or a host cell comprising an expressible polynucleotide encoding a tumor antigen or a fragment or a variant thereof.

The method for selecting of the present invention, preferably, may comprise steps in addition to those explicitly mentioned above. For example, further steps may relate, e.g., a cancer sample for step a), or administration of a recombinant virus, a polynucleotide and/or a host cell comprising an expressible polynucleotide encoding a tumor antigen or a fragment or a variant thereof to a cancer sample after step b). Moreover, one or more of said steps may be performed by automated equipment. The method of the present invention, preferably, is an in vitro method, preferably an in vitro method aiding in taking a treatment decision.

As used herein, the term “detecting a tumor antigen” relates to detecting the presence of a tumor antigen in and/or on the surface of a cell, preferably cancer cell. Preferably, detection is qualitative, more preferably semi-quantitative, most preferably quantitative detection. Preferably, detecting is immunologically detecting, preferably by contacting a, preferably isolated, cancer sample or a fraction thereof with at least one antibody binding to the tumor antigen; preferably, said binding is specific binding. As used herein, the term "specific binding" relates to a binding in which other compounds which are not the tumor antigen are bound with an affinity at least 100 fold, more preferably at least 1000 fold, most preferably at least $10^4$ fold lower as compared to the affinity for the tumor antigen. Preferred methods of immunologically detecting a tumor antigen are known in the art and include in particular in-situ immunostaining, ELISA and related methods, and immunoblots. As will be understood by the skilled person, expression of a tumor antigen may also be detected by detecting an RNA encoding said tumor antigen expressed by a tumor cell.

Selection of the agent for treating a subject suffering from cancer, i.e. the specific selection of recombinant virus, polynucleotide and/or host cell comprising an expressible polynucleotide encoding a tumor antigen or a fragment or a variant thereof, will depend on the specific circumstances. Preferably, if it is found that cancer cells in a cancer sample express a tumor antigen, an agent increasing expression of said tumor antigen will be selected. On the other hand, in case it is found that the cancer cells express a mutant form of a polypeptide (e.g. a neoantigen), preferably, an agent inducing expression of said mutant form will be elected. Thus, preferably the tumor antigen or fragment or variant thereof encoded by the expressible polynucleotide comprised in the recombinant virus, the polynucleotide and/or the host cell selected in step b) shares at least one epitope with the tumor antigen detected in step a). Also preferably, the tumor antigen or fragment or variant thereof encoded by the expressible polynucleotide comprised in the recombinant virus, the polynucleotide and/or the host cell selected in step b) is or is derived from the tumor antigen detected in step a).

In view of the above, the following embodiments are particularly proposed:

EMBODIMENTS

1. A recombinant virus of the family Paramyxoviridae comprising an expressible polynucleotide encoding at least one of (i) a tumor antigen, (ii) a fragment of a tumor antigen, and (iii) a variant of (i) or (ii).

2. The recombinant virus of the family Paramyxoviridae of embodiment 1, wherein said tumor antigen is selected from the group consisting of L-dopachrome-tautomerase (TRP2), melanocyte protein PMEL (gp100), HPV E6/7, MAGE 1, MAGE 3, NY-ESO, androgen receptor (AR), BCL-1, calprotectin, carcinoembryonic antigen (CEA), EGFRs, epithelial cell adhesion molecule (Ep-CAM), epithelial sialomucin, membrane estrogen receptors (mER), FAP HER2/neu, human high molecular weight melanoma-associated antigen (HMW-MAA), IL-6, MOC-1, MOC-21, MOC-52, melan-A/MART-1, melanoma-associated antigen, mucin, OKT9, progesterone receptor (PGR), prostate specific antigen (PSA), prostate stem cell antigen (PSCA), prostate-specific membrane antigen (PSMA), symaptophysin, VEGFRs, CD19, CD20, CD22, CD30 and CD33. More preferably, the tumor antigen is HPV E6, HPVE7, MAGE 1, MAGE 3, NY-ESO, TRP2 or gp100, more preferably is TRP2.

3. The recombinant virus of the family Paramyxoviridae of embodiment 1 or 2, wherein said tumor antigen is a human tumor antigen.

4. The recombinant virus of the family Paramyxoviridae of any one of embodiments 1 to 3, wherein said fragment comprises at least five, preferably at least six, more preferably at least seven, even more preferably at least eight, most preferably at least nine amino acids, wherein preferably, said amino acids correspond to a contiguous sequence comprised in the amino acid sequence of said tumor antigen.

5. The recombinant virus of the family Paramyxoviridae of any one of embodiments 1 to 4, wherein said fragment comprises at least one antigenic epitope of said tumor antigen.

6. The recombinant virus of the family Paramyxoviridae of embodiment 5, wherein said epitope is an MHC class I epitope and/or an MHC class II epitope.

7. The recombinant virus of the family Paramyxoviridae of any one of embodiments 1 to 6, wherein said fragment is selected from the group consisting of (i) a fragment of a human papillomavirus (HPV) E6 polypeptide, preferably of an E6 polypeptide of a high-risk HPV, e.g. of a HPV16 E6 (Genbank Acc No: NP_041325.1 GI: 9627104), (ii) a fragment of a HPV E7 polypeptide, preferably of an E7 polypeptide of a high-risk HPV, e.g. of a HPV16 E7 (Genbank Acc No: NP 041326.1 GI: 9627105); (iii) TRP2, preferably human TRP2 (preferably. encoded by Genbank Acc No: NM_001922.4 GI: 1015809739), (iv) cancer/testis antigen 1B (CTAG1B, also referred to as NY-ESO, preferably encoded by Genbank Acc No: NM_001327.2 GI:215272337, an (v) an arbitrary combination of any of (i) to (iv).

8. The recombinant virus of the family Paramyxoviridae of any one of embodiments 1 to 7, wherein said tumor antigen, fragment or variant thereof comprises, preferably consists of, at least one of (i) a HPV E6 polypeptide, preferably of an E6 polypeptide of a high-risk HPV, e.g. of a HPV16 E6 (Genbank Acc No: NP 041325.1 GI: 9627104), (ii) a HPV E7 polypeptide, preferably of an E7 polypeptide of a high-risk HPV, e.g. of a HPV16 E7 (Genbank Acc No: NP 041326.1 GI: 9627105); (iii) TRP2, preferably human TRP2 (preferably. encoded by Genbank Acc No: NM 001922.4 GI: 1015809739), (iv) cancer/testis antigen 1B (CTAG1B, also referred to as NY-ESO, preferably encoded by Genbank Acc No: NM_001327.2 GI: 215272337), and (v) an arbitrary combination of any of (i) to (iv).

9. The recombinant virus of the family Paramyxoviridae of any one of embodiments 1 to 8, wherein said expressible polynucleotide encodes at least one further of (i) a tumor antigen, (ii) a fragment of a tumor antigen, and (iii) a variant of (i) or (ii).

10. The recombinant virus of the family Paramyxoviridae of any one of embodiments 1 to 9, wherein said expressible polynucleotide is comprised in the genome of said recombinant virus, preferably in a region corresponding to the region intervening the H and the L gene of measles virus.

11. The recombinant virus of the family Paramyxoviridae of any one of embodiments 1 to 10, further comprising at least one expressible polynucleotide encoding a further activator of the immune response.

12. The recombinant virus of the family Paramyxoviridae of embodiment 11, wherein said further activator of the immune response comprises, preferably is, an immunoglobulin or fragment thereof.

13. The recombinant virus of the family Paramyxoviridae of embodiments 11 or 12, wherein said further activator of the immune response comprises, preferably is, a secreted soluble activator of the immune response, preferably IL-12.

14. The recombinant virus of the family Paramyxoviridae of any one of embodiments 11 to 13, wherein said further activator of the immune response comprises, preferably is, a secreted immunoglobulin or fragment thereof.

15. The recombinant virus of the family Paramyxoviridae of any one of embodiments 11 to 14, wherein said further activator of the immune response comprises, preferably is, a single-chain antibody or a nanobody.

16. The recombinant virus of the family Paramyxoviridae of any one of embodiments 11 to 15, wherein said further activator of the immune response comprises, preferably is, a secreted soluble anti-PD-1/PD-L1 antibody.

17. The recombinant virus of the family Paramyxoviridae of any one of embodiments 1 to 16, wherein said recombinant virus is a recombinant Morbillivirus, preferably, a recombinant measles virus (MV).

18. The recombinant virus of the family Paramyxoviridae of any one of embodiments 1 to 17, wherein said recombinant MV is derived from MV strain Edmonston A or B, preferably B, more preferably from MV vaccine strain Schwarz/Moraten.

19. The recombinant virus of the family Paramyxoviridae of any one of embodiments 1 to 18, wherein said at least one expressible polynucleotide is comprised in a polynucleotide encoding the recombinant virus of the family Paramyxoviridae.

20. The recombinant virus of the family Paramyxoviridae of any one of embodiments 1 to 19, wherein said polynucleotide encoding the recombinant virus of the family Paramyxoviridae comprises, preferably consists of, the nucleic acid sequence of any one of SEQ ID NOs: 3 to 5.

21. A polynucleotide encoding the recombinant virus of the family Paramyxoviridae according to any one of embodiments 1 to 20.

22. The polynucleotide according to embodiment 21, wherein said polynucleotide comprises, preferably consists of, the nucleic acid sequence any one of SEQ ID NOs: 3 to 5.

23. A host cell comprising the recombinant virus of the family Paramyxoviridae according to any one of embodiments 1 to 20 and/or the polynucleotide encoding the recombinant virus of the family Paramyxoviridae according to embodiment 21 or 22.

24. The host cell of embodiment 23, wherein said host cell is a cancer cell.

25. A medicament comprising (a) (i) a recombinant virus of the family Paramyxoviridae according of any one of embodiments 1 to 20, (ii) a polynucleotide encoding the recombinant virus of the family Paramyxoviridae according to (i), preferably a polynucleotide according to embodiment 21 or 22;

(iii) a host cell comprising the recombinant virus of the family Paramyxoviridae according to (i) and/or a polynucleotide encoding the recombinant virus of the family Paramyxoviridae according to (ii); preferably a host cell according to embodiment 23 or 24; or (iv) any combination of (i) to (iii); and (b) at least one pharmacologically acceptable excipient.

26. A method for activating immune cells with antitumor activity in a sample comprising cancer cells and immune cells, comprising a) contacting said sample comprising cancer cells and immune cells with (i) a recombinant virus of the family Paramyxoviridae according to any one of embodiments 1 to 20, (ii) a polynucleotide encoding the recombinant virus of the family Paramyxoviridae according to (i), preferably a polynucleotide according to embodiment 21 or 22;

(iii) a host cell comprising the recombinant virus of the family Paramyxoviridae according to (i) and/or a polynucleotide encoding the recombinant virus of the family Paramyxoviridae according to (ii); preferably a host cell according to embodiment 23 or 24; or (iv) any combination of (i) to (iii); and thereby, b) activating immune cells with antitumor activity comprised in said sample.

27. The method of embodiment 26, wherein said method is an in vitro method.

28. A method for treating cancer in a subject afflicted with cancer, comprising a) contacting said subject with (i) a recombinant virus of the family Paramyxoviridae according to any one of embodiments 1 to 20, (ii) a polynucleotide encoding the recombinant virus of the family Paramyxoviridae according to (i), preferably a polynucleotide according to embodiment 21 or 22;

(iii) a host cell comprising the recombinant virus of the family Paramyxoviridae according to (i) and/or a polynucleotide encoding the recombinant virus of the family Paramyxoviridae according to (ii); preferably a host cell according to embodiment 23 or 24; or (iv) any combination of (i) to (iii); and, thereby, b) treating cancer in a subject afflicted with cancer.

29. The method of embodiment 28, wherein said cancer is a solid cancer, a metastasis, or a relapse thereof.

30. The method of embodiment 28 or 29, wherein treating cancer is reducing tumor burden.

31. The method of any one of embodiments 28 to 30, wherein said cancer is malignant melanoma, head and neck cancer, hepatocellular carcinoma, pancreatic carcinoma, prostate cancer, renal cell carcinoma, gastric carcinoma, colorectal carcinoma, a lymphoma or a leukemia.

32. The method of any one of embodiments 28 to 31, wherein said method further comprises the steps of the method for activating immune cells with antitumor activity in a sample according to embodiment 26, and the further step of administering said activated immune cells with antitumor activity to said subject.

33. A preparation of activated immune cells with antitumor activity obtained or obtainable by the method of embodiment 26 or 27.

34. Use of (i) a recombinant virus of the family Paramyxoviridae according to any one of embodiments 1 to 20, (ii) a polynucleotide encoding the recombinant virus of the family Paramyxoviridae according to (i), preferably a polynucleotide according to embodiment 21 or 22;

(iii) a host cell comprising the recombinant virus of the family Paramyxoviridae according to (i) and/or a polynucleotide encoding the recombinant virus of the family Paramyxoviridae according to (ii); preferably a host cell according to embodiment 23 or 24; or (iv) any combination of (i) to (iii);

for the manufacture of a medicament, preferably for the manufacture of a medicament for treating inappropriate cell proliferation.

35. A recombinant virus of the family Paramyxoviridae according to any one of embodiments 1 to 20 and/or a polynucleotide according to embodiment 21 or 22 and/or a host cell according to embodiment 23 or 24 for use in medical treatment.

36. A recombinant virus of the family Paramyxoviridae according to any one of embodiments 1 to 20 and/or a polynucleotide according to embodiment 21 or 22 and/or a host cell according to embodiment 23 or 24 for use in treatment of inappropriate cell proliferation.

37. The recombinant virus of the family Paramyxoviridae for use of embodiment 36, wherein treatment of inappropriate cell proliferation is cancer treatment.

38. A kit comprising (i) a recombinant virus of the family Paramyxoviridae according of any one of embodiments 1 to 20, (ii) a polynucleotide encoding the recombinant virus of the family Paramyxoviridae according to (i), preferably a polynucleotide according to embodiment 21 or 22;

(iii) a host cell comprising the recombinant virus of the family Paramyxoviridae according to (i) and/or a polynucleotide encoding the recombinant virus of the family Paramyxoviridae according to (ii); preferably a host cell according to embodiment 23 or 24; or (iv) any combination of (i) to (iii);

housed in a container.

39. A method for selecting (i) a recombinant virus of the family Paramyxoviridae comprising an expressible polynucleotide encoding a tumor antigen or a fragment or variant thereof, (ii) a polynucleotide encoding the recombinant virus of (i), and/or (iii) a host cell comprising the recombinant virus according to (i) and/or a polynucleotide according to (ii) for treating a subject suffering from cancer, said method comprising a) detecting at least one tumor antigen expressed by cancer cells in a cancer sample of said subject; and, b) based on the determination of step a), selecting a recombinant virus, a polynucleotide and/or a host cell comprising an expressible polynucleotide encoding a tumor antigen or a fragment or a variant thereof.

40. The method of embodiment 39, wherein the tumor antigen or fragment or variant thereof encoded by the expressible polynucleotide comprised in the recombinant virus, the polynucleotide and/or the host cell selected in step b) shares at least one epitope with the tumor antigen detected in step a).

41. The method of embodiment 39 or 40, wherein the tumor antigen or fragment or variant thereof encoded by the expressible polynucleotide comprised in the recombinant virus, the polynucleotide and/or the host cell selected in step b) is or is derived from the tumor antigen detected in step a).

42. The method of any one of embodiments 39 to 41, wherein the recombinant virus of (i) is a recombinant virus according to any one of embodiments 1 to 20, wherein the polynucleotide of (ii) is a polynucleotide according to embodiment 21 or 22, and/or wherein the host cell of (iii) is a host cell according to embodiment 23 or 24.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

EXAMPLE 1

Figure 1:
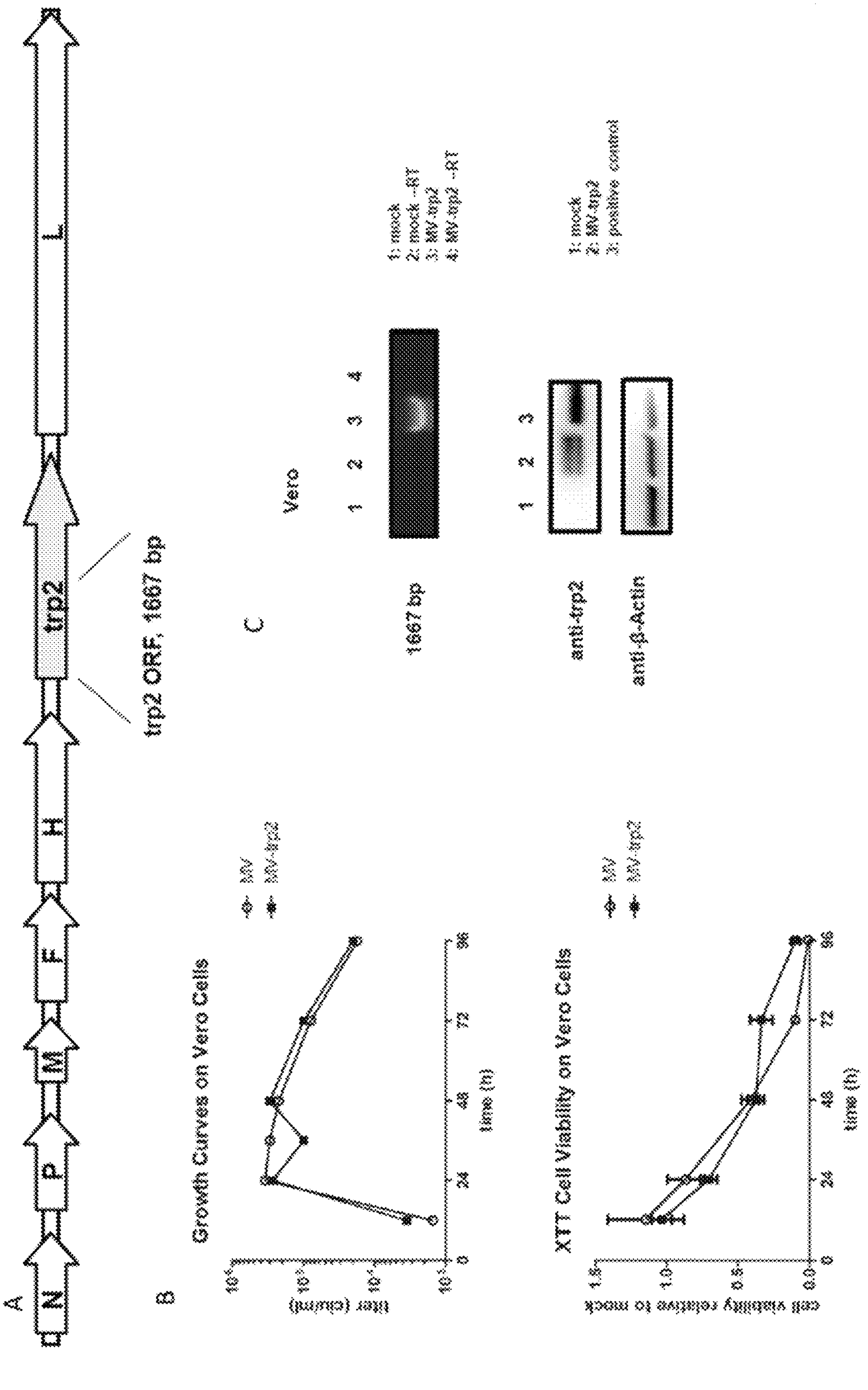
FIG. 1: A) Schematic representation of the recombinant MV genome. cDNA encoding trp2 (1667 bp) was inserted into the MeV Schwarz genome into an additional transcription unit downstream of the hemagglutinin open reading frame. B) Upper panel: growth of measles virus constructs (MV-trp2 or MV (control)) on Vero cells; x-axis: time (hours), y-axis: titer (cell infectious units (ciu)/ml); lower panel: viability of host cells over the course of MV-trp2 and MV (control) replication, as compared to a mock-infected culture; x-axis: Time (hours), y-axis: relative viability compared to mock infected culture. C) Expression of trp2 by MV-trp2, but not by MV; upper panel: RT-PCR with trp2-specific primers; lower panel: immunoblot with anti-trp2 antibodies.

Recombinant measles viruses encoding the tumor-associated antigen (TAA) trp2 have been generated according to known methods (MV-trp2, FIG. 1A).

Vero cells were transduced with parental MV or MV encoding trp2 with a multiplicity of infection (MOI)=3. At designated time points, cells were harvested and progeny viral particles were determined in titration assays by serial dilution. Insertion of the tumor-associated antigen does not impair viral replication and cytotoxic effects (FIG. 1B, upper panel). At designated time points, cell viability was determined using a colorimetric XTT assay (FIG. 1B, lower panel). Mock treated cells were used as a reference for viability=1.0.

RNA was extracted from Vero cells infected with parental MV or MV encoding trp2. cDNA synthesis was performed using oligo-dT primers. PCR was performed with trp2-specific primers. Cells infected with parental MV or MV encoding trp2 were lysed in RIPA buffer for protein extraction. After SDS PAGE of cell lysates, Western blot analysis was performed with trp2-specific antisera. Beta-actin was detected as a loading control. A melanosome preparation was used as a positive control. Tumor-antigen expression in infected cells was confirmed both on the mRNA- and protein level (FIG. 1C).

EXAMPLE 2

Figure 2:
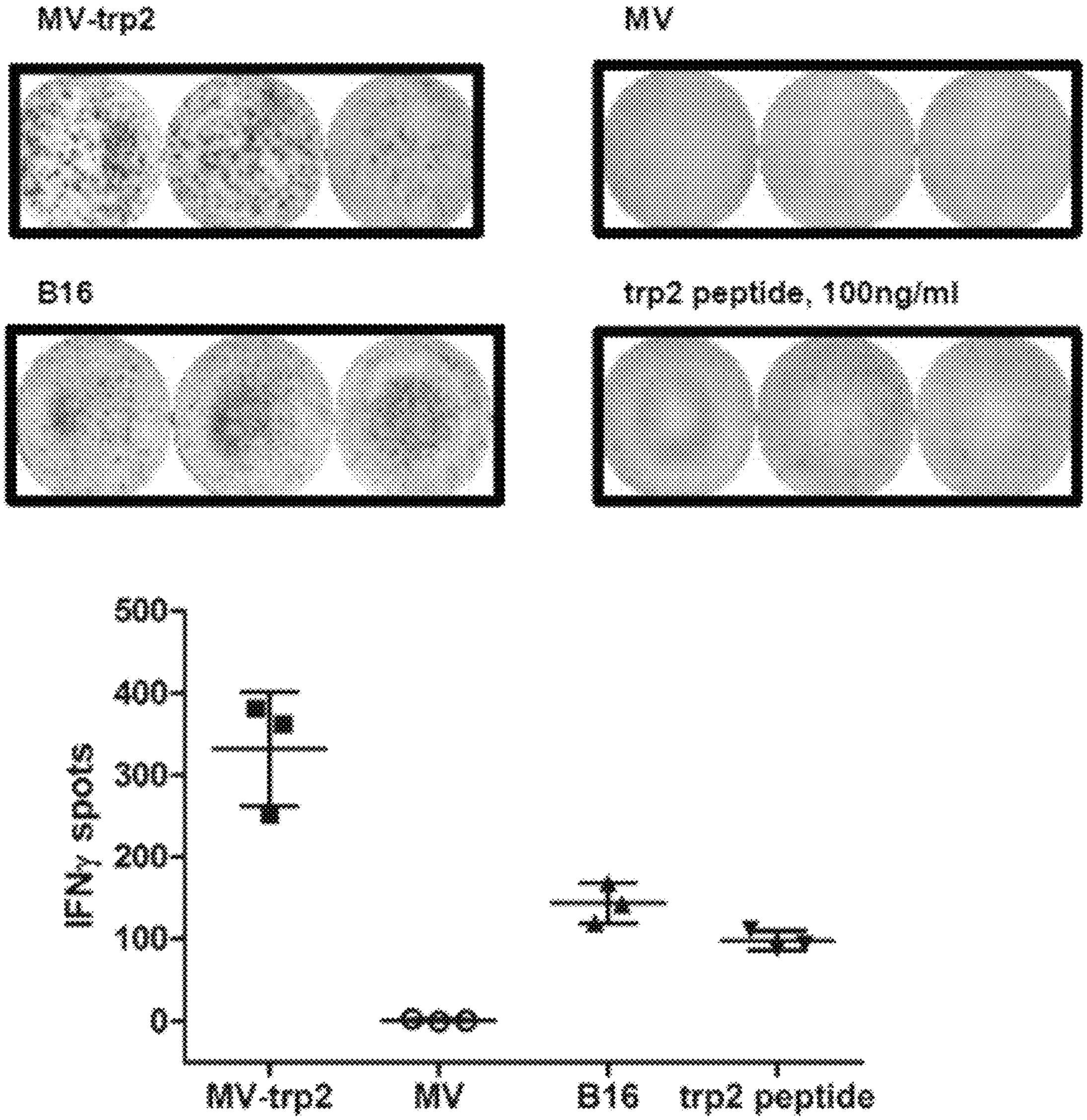
FIG. 2: IFN-gamma ELISPOT analysis of co-cultures described in Example 2; upper panels: photographs of culture dishes after ELISPOT assay; lower graph: quantification of the spots in culture dishes as shown in the upper panels.

Trp2-specific T cells were co-cultured with MC38-hCD46 cells infected with MV-trp2 or parental MV or with B16 cells or stimulated with the immunodominant trp2 peptide. After 16 hours of co-culture, IFN-gamma ELISPOT analysis was performed. MV encoding the trp2 tumor antigen (TAA) activate TAA-specific T cells: Co-culture of trp2-specific T cells with murine cells infected with MV-trp2 leads to significantly higher IFN-gamma secretion than co-culture with parental MV (FIG. 2).

EXAMPLE 3

$1\times10^6$ B16ova_hCD46 cells were implanted into the flank of C57BL/6J mice (day 0). Starting on day 10, mice received intratumoral injections of $1\times10^6$ cell infectious units (ciu) of MV-trp2, $1\times10^6$ ciu of parental MV in a total volume of 100 μL or 100 μL carrier fluid (mock). Mice were sacrificed on day 23 and spleens were extracted for ELISPOT analysis.

Figure 3:
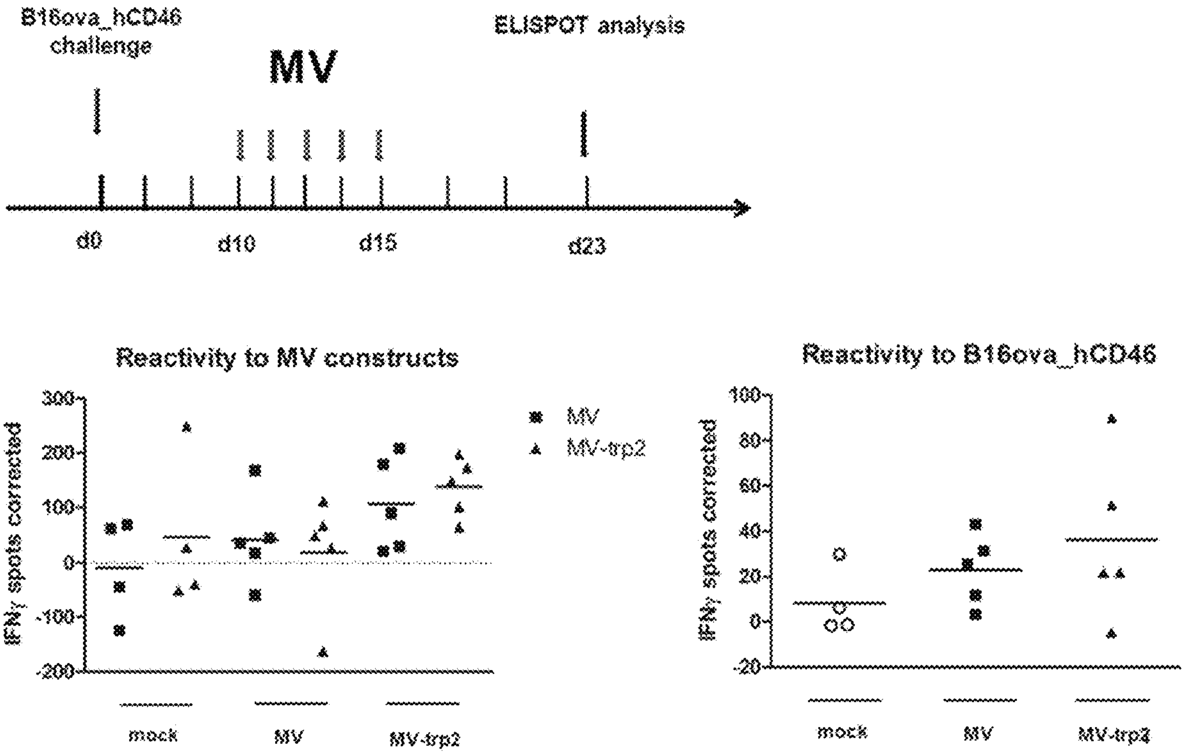
FIG. 3: Eliciting anti-tumor immunity in mice by intratumoral injection of MV-trp2 (Example 3); upper panel: Treatment schedule; lower left panel: quantification of results of an IFN-gamma ELISPOT analysis using splenocytes of mice from different treatment groups in co-culture with MC38-hCD46 cells infected with MV-trp2 or parental MV; lower right panel: quantification of results of an IFN-gamma ELISPOT analysis using splenocytes of mice from different treatment groups in co-culture with B16 cells.

Splenocytes of mice from different treatment groups were co-cultured with MC38-hCD46 cells infected with MV-trp2 or parental MV. After 16 hours of co-culture, IFN-gamma ELISPOT analysis was performed. Splenocytes of mice from different treatment groups were co-cultured with B16 cells. After 16 hours of co-culture, IFN-gamma ELISPOT analysis was performed. It was found that intratumoral injection of MV-trp2 can enhance TAA-specific and tumor-specific immunity (FIG. 3).

Thus, in the present invention, an oncolytic MV vaccine was generated to elicit a tumour antigen-specific immune response. With this approach, the MV vector encoded tumour antigen is expressed in the context of viral danger-associated molecular patterns (DAMPs) and pathogen-associated molecular patterns (PAMPs) which serve as "natural adjuvants". Furthermore, MV-mediated oncolysis functions as an in situ tumour vaccine: MV infection causes immunogenic cell death within the tumour accompanied by release of tumour-associated antigens, resulting in efficient antigen cross-presentation and epitope spread.

What is claimed is:

1. A replication competent recombinant virus of the family Paramyxoviridae encoded by an expressible polynucleotide comprising the nucleic acid sequence of any one of SEQ ID NOs: 3 to 5.

2. The replication competent recombinant virus of the family Paramyxoviridae of claim 1, in which the nucleic acid sequence of the expressible polynucleotide further encodes a further activator of the immune response.

3. A polynucleotide encoding the replication competent recombinant virus of the family Paramyxoviridae according to claim 1.

4. A host cell comprising the replication competent recombinant virus of the family Paramyxoviridae according to claim 1 or a polynucleotide according to claim 3.

5. A method for activating immune cells with antitumor activity in a sample comprising cancer cells and immune cells, comprising a) contacting said sample comprising cancer cells and immune cells with (i) a replication competent recombinant virus of the family Paramyxoviridae according to claim 1, (ii) a polynucleotide encoding the replication competent recombinant virus of the family Paramyxoviridae according to (i);

(iii) a host cell comprising the replication competent recombinant virus of the family Paramyxoviridae according to (i) or the polynucleotide encoding the replication competent recombinant virus of the family Paramyxoviridae according to (ii); or (iv) any combination of (i) to (iii); and thereby, b) activating immune cells with antitumor activity comprised in said sample.

6. A medicament comprising:

(i) a replication competent recombinant virus of the family Paramyxoviridae according to claim 1, (ii) a polynucleotide encoding the replication competent recombinant virus of the family Paramyxoviridae according to (i);

(iii) a host cell comprising the replication competent recombinant virus of the family Paramyxoviridae according to (i) or the polynucleotide encoding the replication competent recombinant virus of the family Paramyxoviridae according to (ii); or (iv) any combination of (i) to (iii).

7. The medicament of claim 6, wherein the medicament is for the treatment of inappropriate cell proliferation.

8. A kit comprising (i) a replication competent recombinant virus of the family Paramyxoviridae according of claim 1, (ii) a polynucleotide encoding the replication competent recombinant virus of the family Paramyxoviridae according to (i);

(iii) a host cell comprising the replication competent recombinant virus of the family Paramyxoviridae according to (i) or the polynucleotide encoding the replication competent recombinant virus of the family Paramyxoviridae according to (ii); or (iv) any combination of (i) to (iii);

housed in a container.

9. The medicament of claim 7, wherein the inappropriate cell proliferation is cancer.

* * * * *